US012037430B2

(12) United States Patent
Takeuchi et al.

(10) Patent No.: US 12,037,430 B2
(45) Date of Patent: Jul. 16, 2024

(54) TARGET SUBSTANCE POLYMER REPLICA SUBSTRATE, METHOD FOR PRODUCING SAME, AND METHOD FOR PRODUCING SUBSTRATE SENSOR

(71) Applicants: National University Corporation Kobe University, Kobe (JP); Murata Manufacturing Co., Ltd., Nagaokakyo (JP)

(72) Inventors: Toshifumi Takeuchi, Kobe (JP); Hirobumi Sunayama, Kobe (JP); Eri Takano, Kobe (JP)

(73) Assignees: National University Corporation Kobe University, Kobe (JP); Murata Manufacturing Co., Ltd., Nagaokakyo (JP)

( * ) Notice: Subject to any disclaimer, the term of this patent is extended or adjusted under 35 U.S.C. 154(b) by 657 days.

(21) Appl. No.: 17/285,829

(22) PCT Filed: Sep. 4, 2019

(86) PCT No.: PCT/JP2019/034855
§ 371 (c)(1),
(2) Date: Apr. 15, 2021

(87) PCT Pub. No.: WO2020/079979
PCT Pub. Date: Apr. 23, 2020

(65) Prior Publication Data
US 2021/0388139 A1      Dec. 16, 2021

(30) Foreign Application Priority Data

Oct. 17, 2018   (JP) .................................. 2018-195918

(51) Int. Cl.
*G01N 33/53*      (2006.01)
*C07K 17/08*      (2006.01)
(Continued)

(52) U.S. Cl.
CPC .......... *C08F 222/385* (2013.01); *C07K 17/08* (2013.01); *C08F 8/00* (2013.01);
(Continued)

(58) Field of Classification Search
CPC ................. G01N 33/53; G01N 33/531; G01N 33/54366; G01N 33/543
See application file for complete search history.

(56) References Cited

U.S. PATENT DOCUMENTS

2020/0110084 A1   4/2020   Takeuchi et al.

FOREIGN PATENT DOCUMENTS

| JP | 2006-137805 A | 6/2006 |
| JP | 2017-019992 A | 1/2017 |
| WO | WO 2018/221271 A1 | 12/2018 |

OTHER PUBLICATIONS

International Search Report in PCT/JP2019/034855 issued Nov. 12, 2019.

*Primary Examiner* — Caixia Lu
(74) *Attorney, Agent, or Firm* — Knobbe, Martens, Olson and Bear, LLP

(57) ABSTRACT

The present invention provides a polymer replica of a target molecule, the polymer replica being capable of accurately inheriting surface information possessed by the target molecule in a molecular imprinting technique. A polymer replica of a target substance, the target substance having multiple types of binding groups including at least a binding group BG1 and a binding group BG2 on the surface, wherein: the polymer replica is configured from a second molecularly imprinted polymer having, as a template, a first molecularly imprinted polymer having the target substance as a template; the polymer replica has on the surface thereof at least a binding group bg1 at a position corresponding to the position of binding group BG1 and a binding group bg2 at a position corresponding to the position of the binding group
(Continued)

BG2 on the surface of the target substance; and the polymer replica of the target substance can be used as a template during synthesis of a molecularly imprinted polymer having a specific recognition site for the target substance because the polymer replica accurately inherits the surface information possessed by the target molecule.

15 Claims, 6 Drawing Sheets

(51) Int. Cl.
    *C08F 8/00*           (2006.01)
    *C08F 220/06*       (2006.01)
    *C08F 220/56*       (2006.01)
    *C08F 222/38*       (2006.01)
    *G01N 33/531*      (2006.01)
    *G01N 33/543*      (2006.01)

(52) U.S. Cl.
    CPC .......... *C08F 220/06* (2013.01); *C08F 220/56* (2013.01); *G01N 33/53* (2013.01); *G01N 33/531* (2013.01); *G01N 33/543* (2013.01); *G01N 33/54366* (2013.01); *C08F 2438/01* (2013.01)

AFP (Target substance)

<STEP 1>

TARGET SUBSTANCE POLYMER REPLICA SUBSTRATE, METHOD FOR PRODUCING SAME, AND METHOD FOR PRODUCING SUBSTRATE SENSOR

TECHNICAL FIELD

The present invention relates to a polymer replica substrate of a target substance, a method for producing the polymer replica substrate, and a method for producing a substrate sensor.

BACKGROUND ART

A molecularly imprinted polymer (MIP) is a synthetic polymer prepared by accumulating monomer molecules around a target molecule as a template, copolymerizing the monomer molecules with a crosslinking agent, and then washing away the target molecule as a template. A MIP has a space formed with a template for molecular imprinting, and is expected as an artificial material that replaces an antibody by the specific recognition of the target molecule in the space.

For example, Patent document 1 describes a specific example of a method of preparing a molecularly imprinted polymer that is a method for producing a molecularly imprinted polymer having a specific recognition space for a target protein, the method including the steps of: bonding, through a reactive group (1) of a molecule included in the target protein, a plurality of functional monomers (I) each having a vinyl monomer group at a terminal and having a cleavable group (1) at a portion other than the terminal (here, the cleavable group (1) is a disulfide-bonding group, an imino-bonding group, a boronate-cis-diol ester group, or a carboxylic acid ester group); bonding, through a reactive group (2) of a molecule included in the target protein, a plurality of functional monomers (II) each having a vinyl monomer group at a terminal and having a cleavable group (2) at a portion other than the terminal (here, the cleavable group (2) is a disulfide-bonding group, an imino-bonding group, a boronate-cis-diol ester group, or a carboxylic acid ester group other than the cleavable group (1)); forming a self-assembled monolayer on a substrate; bonding the target protein to a surface of the self-assembled monolayer; adding a vinyl monomer and copolymerizing the vinyl monomer with the vinyl monomer group of the functional monomer (I) and the vinyl monomer group of the functional monomer (II); removing the target protein by cleaving at least the cleavable group (1) and the cleavable group (2); bonding a plurality of post-imprinting compounds capable of interacting with the reactive group (1) to a group generated by cleaving the cleavable group (1), or bonding a plurality of post-imprinting compounds capable of interacting with the reactive group (2) to a group generated by cleaving the cleavable group (2); and bonding a plurality fluorescent reporter compounds to a group generated by cleaving the cleavable group (1) or a group generated by cleaving the cleavable group (2) that is not bonded to the post-imprinting compound. The molecularly imprinted polymer thus prepared to have a specific recognition space for the target protein is expected to be used as a substrate sensor or the like.

PRIOR ART DOCUMENT

Patent Document

Patent document 1: Japanese Patent Laid-open Publication No. 2017-19992

SUMMARY OF THE INVENTION

Problems to be Solved by the Invention

In preparation of a MIP, a purified target molecule is used as a template. However, a target molecule is generally expensive and difficult to obtain. Even so, a target molecule is usually used once and then thrown away because it is unstable and, in addition, subjected to treatment such as decomposition in the step of removing after used as a template for synthesis of a MIP. For this reason, the efficiency of producing the sensor substrate is extremely low. As a result, the substrate sensor itself including the MIP of the target molecule is rare and expensive, so that the substrate sensor is far from being mass-produced.

For a saving of a target molecule as a template, the present inventors focused on a method in which molecular imprinting technique is used to obtain a polymer replica of the target molecule, and the polymer replica is used in place of the target molecule and utilized as an artificial template.

A specific method can be considered in which a target molecule as a template is used for preparing a MIP (first imprinted polymer) having a recess-shaped molecular imprinting space, and the recess-shaped molecular imprinting space is used as a template for further molecular imprinting to obtain a polymer replica of the target molecule as a protrusion-shaped MIP (second imprinted polymer) by the further molecular imprinting.

However, even if the polymer replica as a template is used for preparing a substrate sensor by further molecular imprinting, the surface information (the positional information and the qualitative information of the functional group) of the original target molecule is no longer accurately inherited after sequential molecular imprinting processes in which the MIPs are used as a template. As a result, the substrate sensor prepared using the polymer replica as a template has low sensitivity finally.

Therefore, an object of the present invention is to provide a polymer replica of a target molecule, the polymer replica capable of accurately inheriting the surface information (the positional information and the qualitative information of the functional group) of the target molecule in molecular imprinting technique.

Means for Solving the Problem

As a result of intensive studies, the present inventors have found that the surface information (the positional information and the qualitative information of the functional group) of a template can be accurately copied on a MIP by treating each object to be used as a template in sequential molecular imprinting processes as follows. First, a vinyl group is introduced into a binding group on the template that is the key to the surface information through a reversible linking group, and then in the molecular imprinting process, the vinyl group introduced into the template is copolymerized with a monomer. The present invention has been completed by further studies based on the above-described findings. That is, the present invention provides an invention having the aspects described below.

Item 1. A polymer replica of a target substance, the target substance having a plurality of kinds of binding groups including at least a binding group BG1 and a binding group BG2 on a surface, the polymer replica including a second molecularly imprinted polymer produced using a first molecularly imprinted polymer as a template, the first molecularly imprinted polymer produced using the target substance as a template, the polymer replica having, on a surface, at least a binding group bg1 at a position corresponding to a position of the binding group BG1 on the surface of the target substance; and a binding group bg2 at a position corresponding to a position of the binding group BG2 on the surface of the target substance.

Item 2. The polymer replica of the target substance according to Item 1, further including a substrate and a polymer film having a protrusion, the polymer film provided on a surface of the substrate, the protrusion including the second molecularly imprinted polymer.

Item 3. The polymer replica of the target substance according to Item 1 or 2, wherein the target substance is a protein, the binding group BG1 and the binding group BG2 are at least two kinds of groups selected from the group consisting of a carboxyl group, an amino group, and sugar groups, and the binding group bg1 and the binding group bg2 are at least two kinds of groups selected from the group consisting of a carboxyl group, a thiol group, and sugar groups.

Item 4. A method for producing a polymer replica of a target substance, the method including:

a step 1 of bonding a functional monomer FM1 having a vinyl group and a reversible linking group RV1 to a target substance having a plurality of kinds of binding groups on a surface through at least a binding group BG1 among the plurality of kinds of binding groups;

a step 2 of reacting a binding group BG2 among the plurality of kinds of binding groups on a substrate S1 and immobilizing the target substance through a reversible linking group RV2;

a step 3 of performing molecular imprinting by adding a vinyl monomer onto the substrate S1 and copolymerizing the vinyl monomer with the vinyl group;

a step 4 of cleaving the reversible linking group RV1 and the reversible linking group RV2 and removing the target substance to obtain a first molecularly imprinted polymer that includes a recess generated using the target substance as a template and includes a binding group bg1' and a binding group bg2' on a surface of the recess, the binding group bg1' and the binding group bg2' each being a cleavage residue;

a step 5 of reacting the binding group bg1' of the first molecularly imprinted polymer with a functional monomer FM51 that has a reactive group capable of reacting with the binding group bg1' to form a reversible linking group RV1 and has a vinyl group, and reacting the binding group bg2' of the first molecularly imprinted polymer with a functional monomer FM52 that has a reactive group capable of reacting with the binding group bg2' to form a reversible linking group RV2 and has a vinyl group;

a step 6 of performing molecular imprinting by adding a vinyl monomer onto the first molecularly imprinted polymer and copolymerizing the vinyl monomer with the vinyl group of the functional monomer FM51 and with the vinyl group of the functional monomer FM52; and a step 7 of cleaving the reversible linking group RV1 and the reversible linking group RV2 and removing the first molecularly imprinted polymer to obtain a second molecularly imprinted polymer having a binding group bg1 and a binding group bg2, the binding group bg1 and the binding group bg2 each being a cleavage residue.

Item 5. The method according to Item 4, wherein the step 6 is a step of performing molecular imprinting by adding the vinyl monomer onto the first molecularly imprinted polymer, laminating the first molecularly imprinted polymer with a substrate S2 through the vinyl monomer, and copolymerizing the vinyl monomer with the vinyl group of the functional monomer FM51 and with the vinyl group of the functional monomer FM52, and the step 7 is a step of cleaving the reversible linking group RV1 and the reversible linking group RV2 and removing the first molecularly imprinted polymer to obtain a second molecularly imprinted polymer having the substrate S2 and having a binding group bg1 and a binding group bg2 on a surface of the substrate S2, the binding group bg1 and the binding group bg2 each being a cleavage residue.

Item 6. The method according to Item 4, wherein the target substance is a protein, in the step 3, the vinyl monomer contains a functional monomer FM3 having a basic group and a vinyl group, and in the step 6, the vinyl monomer contains a functional monomer FM6 having an acidic group bg3 and a vinyl group.

Item 7. The method according to any one of Items 4 to 6, wherein the binding group BG1 is an amino group.

Item 8. The method according to any one of Items 4 to 7, wherein the reversible linking group RV1 is a disulfide group, and the binding group bg1 is a thiol group.

Item 9. The method according to any one of Items 4 to 8, wherein the protein is a glycoconjugate, and the binding group BG2 is a sugar group, the reversible linking group RV2 is a boronate-cis-diol ester group, and the binding group bg2 is a boronic acid group.

Item 10. A polymer replica of a target substance, the polymer replica produced by the method according to any one of Items 4 to 9.

Item 11. A method for producing a substrate sensor, the method including:

a step 11 of, on a surface of the second molecularly imprinted polymer on the substrate of the polymer replica of the target substance, the polymer replica according to Item 2, or the polymer replica of the target substance, the polymer replica produced by the method according to any one of Items 5 to 9, reacting the binding group bg1 with a functional monomer FM111 that has a reactive group capable of reacting with the binding group bg1 to form a reversible linking group RV1 and has a vinyl group, and reacting the binding group bg2 with a functional monomer FM112 that has a reactive group capable of reacting with the binding group bg2 to form a reversible linking group RV2 and has a vinyl group;

a step 12 of performing molecular imprinting by adding a vinyl monomer onto the second molecularly imprinted polymer on the substrate, laminating the second molecularly imprinted polymer with a substrate S3 through the vinyl monomer, and copolymerizing the vinyl monomer with the vinyl group of the functional monomer FM111 and with the vinyl group of the functional monomer FM112;

a step 13 of cleaving the reversible linking group RV1 and the reversible linking group RV2 and separating the substrate of the polymer replica of the target substance to obtain a third molecularly imprinted polymer having the substrate S3, having a recess generated using the second molecularly imprinted polymer as a template, and having a binding group bg1' and a binding group bg2' on a surface of the recess, the binding group bg1' and the binding group bg2' each being a cleavage residue; and a step 14 of bonding a post-imprinting compound and/or a signal substance capable of interacting with at least one of a binding group BG1 or a binding group BG2 to at least one of the binding group bg1' or the binding group bg2'.

Item 12. The method according to Item 11, wherein the target substance is a protein, and in the step 12, the vinyl monomer contains a functional monomer FM12 having a basic group and a vinyl group.

Item 13. The method according to Item 11 or 12, wherein the binding group BG1 is an amino group.

Item 14. The method according to any one of Items 11 to 13, wherein the reversible linking group RV1 is a disulfide group, and the binding group bg1' is a thiol group.

Item 15. The method according to any one of Items 11 to 14, wherein the protein is a glycoconjugate, and the binding group BG2 is a sugar group, the reversible linking group RV2 is a boronate-cis-diol ester group, and the binding group bg2' is a boronic acid group.

Advantages of the Invention

The present invention provides a polymer replica of a target molecule, the polymer replica capable of accurately inheriting the surface information of the target molecule in molecular imprinting technique. Furthermore, molecular imprinting in which the polymer replica of the target molecule is used as an artificial template provides a substrate sensor having high sensitivity to the target molecule.

EMBODIMENTS OF THE INVENTION

[1. Polymer Replica of Target Substance]

Figure 1:
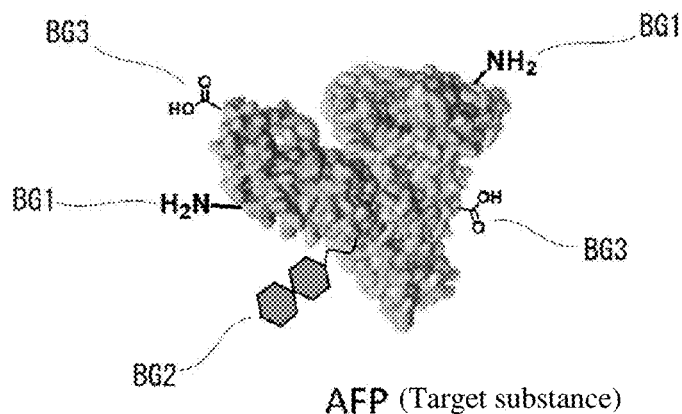
FIG. 1 schematically illustrates a target substance in an embodiment of the present invention.

The polymer replica of a target substance according to the present invention is a synthetic polymer structure copying the functional group information (specifically, the positional information and the qualitative information of the functional group) on the surface of the target substance. FIG. 1 schematically illustrates an example of the target substance (specifically, α-fetoprotein (AFP), which is a biomarker for liver cancer), and FIGS. 2(a) and 2(b) schematically illustrate an example of the polymer replica of the target substance in FIG. 1.

The target substance is not particularly limited as long as it is a substance having a plurality of kinds of binding groups on its surface. In the present invention, the term "binding group" refers to a functional group capable of covalent bond or non-covalent bond formation. Examples of the non-covalent bond include hydrogen bonds, ionic bonds, electrostatic interactions, van der Waals interactions, and hydrophobic interactions. The binding group of the target substance is not particularly limited, and examples of the binding group include basic groups such as an amino group; sugar groups having a cis-diol ester group, such as monosaccharide groups, oligosaccharide groups, and polysaccharide groups; a thiol group; a hydroxyl group, phenolic hydroxyl groups; acidic groups such as a carboxyl group; antigenic determinants having an epitope structure; and aromatic groups such as a phenyl group, an indole group, and an imidazoyl group. In the present invention, binding groups of the target substance are described as a binding group BG1, a binding group BG2, a binding group BG3, and so on. In the present invention, the target substance has at least a binding group BG1 and a binding group BG2 as the plurality of kinds of binding groups. In the present invention, examples of the combination of a binding group of the target substance, a binding group corresponding to the binding group of the target substance, and the kind of a bond formed by the two binding groups are as described below.

TABLE 1

| Binding group of target substance (binding group BG1, BG2, BG3 . . . ) | Binding group corresponding to binding group of target substance | Kind of bond |
|---|---|---|
| Basic groups (such as amino group) | Carboxylic acid active ester groups (active ester groups in which N-hydroxysuccinimide, sodium N-hydroxysulfosuccinimide, nitrophenol, pentafluorophenol, or the like is used; carbamic acid active ester groups such as NHS carbamate); carboxyl group; aldehyde group; isocyanate group; isothiocyanate group; epoxy group; maleimide group, and the like | Covalent bond |
| | Acidic groups (such as carboxyl group and sulfo group) | Non-covalent bond (electrostatic interaction) |
| Sugar groups (cis-diol groups) | Boronic acid group | Covalent bond (boronate-cis-diol ester group) |
| Thiol group | Unsaturated carbon groups lack of electron, such as maleimide group and acrylic acid ester groups; iodoacetamide group; pyridyl disulfide group; alkene (vinyl sulfone)/alkyne groups for radical addition click chemistry; thioester groups for native chemical ligation method, and the like | Covalent bond |
| Hydroxyl group, phenolic hydroxyl groups | Carboxylic acid active ester groups | Covalent bond |
| Acidic groups (such as carboxyl group) | Basic groups (such as amino group, cyclic secondary amino groups (such as pyrrolidyl group and piperidyl group), pyridyl group, imidazole group, and guanidine group), hydroxyl group | Non-covalent bond (hydrogen bond and electrostatic interaction) |
| Antigenic determinants (epitope) | Antibodies, paratopes | Non-covalent bond (intermolecular specific interaction) |
| Aromatic groups (such as phenyl group, indole group, and imidazoyl group) | Aromatic groups (such as phenyl groups such as aminophenyl group, naphthyl groups such as aminonaphthyl group, and pyridyl group) | Non-covalent bond (hydrophobic interaction) |

Specific examples of the target substance include low molecular weight substances and proteins. Examples of the low molecular weight substances include pharmaceuticals, pesticides, and environmental hormones, and examples of the proteins include antibodies, disease markers, vaccines, and enzymes. In the present invention, the proteins also include peptides and glycoproteins to which a sugar group is bonded. The antibodies also include Fab, Fab', F(ab')$_2$, ScFv, and the like. Preferable examples of the target substance include proteins. In the case that the target substance is a protein, the above-described binding group is the side chain of the amino acid residue of the protein. Specific examples of the binding group in such a case include amino groups of residues such as a lysine residue and an N-terminal; carboxy groups of residues such as an aspartic acid residue, a glutamate residue, and a C-terminal; a thiol group of a cysteine residue; hydroxyl groups of residues such as a serine residue and a threonine residue; and a phenolic hydroxyl group of a tyrosine residue. More preferable examples of the target substance include glycoproteins. In the case that the target substance is a protein, the above-described binding group is also the sugar group (cis-diol ester group) of the protein.

The target substance in FIG. 1, AFP has a binding group BG1 (amino group in this example), a binding group BG2 (sugar group in this example), and a binding group BG3 (carboxyl group in this example) as binding groups.

The polymer replica of the target substance in FIG. 2(a) is integrated with a substrate. That is, a protrusion is provided on the substrate, and the protrusion functions as the polymer replica. Specifically, the polymer replica of the target substance shown in FIG. 2(a) includes a substrate S2 and a polymer film that is provided on the surface of the substrate S2 and has a protrusion. The protrusion (polymer replica portion) has, on its surface, a plurality of kinds of binding groups including at least a binding group bg1 (thiol group in this example) and a binding group bg2 (sugar group in this example). The example in FIG. 2(a) is a polymer replica of AFP, which is a glycoprotein, so that the protrusion also has a binding group bg3 (carboxyl group in this example) on its surface. In the polymer replica of the target substance in FIG. 2(a), it is preferable that a plurality of protrusion-shaped polymer replica portions be formed on one substrate S2. The polymer replica of the target substance in FIG. 2(b) has a particle shape.

The polymer replica includes a second molecularly imprinted polymer produced using, as a template, a first molecularly imprinted polymer produced using the target substance in FIG. 1 as a template. That is, the polymer replica is a positive second molecularly imprinted polymer obtained by the following procedure. Molecular imprinting is performed using the target substance in FIG. 1 as a template to obtain a negative first molecularly imprinted polymer, and subsequent molecular imprinting is performed using the first molecularly imprinted polymer as a template to obtain a positive second molecularly imprinted polymer. The second molecularly imprinted polymer included in the polymer replica is produced through two times of molecular imprinting, so that the second molecularly imprinted polymer usually has a shape similar to that of the target substance. The surface shape of the target substance is approximately copied to the second molecularly imprinted polymer.

The polymer replica has a plurality of binding groups on its surface. In the present invention, binding groups of the polymer replica are described as a binding group bg1, a binding group bg2, a binding group bg3, and so on. In the present invention, the polymer replica has at least a binding group bg1 and a binding group bg2 as the plurality of kinds of binding groups. In the examples of FIGS. 2(a) and 2(b), the polymer replica has a binding group bg1 at a position corresponding to the position of the binding group BG1 on the surface of the target substance, a binding group bg2 at a position corresponding to the position of the binding group BG2, and a binding group bg3 at a position corresponding to the position of the binding group BG3.

The state that the binding group bg1 is at a position corresponding to the binding group BG1 refers to the following state (i) or (ii) assuming that the target substance and the polymer replica of the target substance are superposed in a space. (i) The binding group bg1 is at the same or approximately the same position as the binding group BG1 in the space (for example, in the case that a substance s specifically binds to the target substance through the binding group BG1, the binding groups are at the same position so that the substance s can also specifically bind to the polymer replica through the binding group bg1). (ii) Although the spatial position of the binding group bg1 is neither the same nor approximately the same as that of the binding group BG1, the distance between the binding group bg1 and the binding group BG1 is so small that a low molecular weight compound (for example, a post-imprinting compound and/or a signal substance capable of interacting with the binding group BG1, described below) can intermediate between the binding groups. At least one of the plurality of binding groups of the polymer replica of the target substance is at the same or approximately the same position as the binding group of the target substance.

The binding group bg1, the binding group bg2, and the binding group bg3 of the polymer replica shown in FIGS. 2(a) and 2(b) correspond to the binding group BG1, the binding group BG2, and the binding group BG3 of the target substance, respectively. The binding group of the polymer replica may be the same or the same kind as the binding group of the target substance (for example, monosaccharide groups, oligosaccharide groups, and polysaccharide groups are the same kind of groups because they all have sugar as the basic composition, and antibody groups and paratopes are the same kind of groups because they all have an antibody recognition site as the basic composition), or may be different from the binding group of the target substance. In the examples of FIGS. 2(a) and 2(b), the binding group bg1 of the polymer replica is a thiol group, the corresponding binding group BG1 is an amino group, the binding group bg2 of the polymer replica is a monosaccharide group, the corresponding binding group BG2 is a polysaccharide group, the binding group bg3 of the polymer replica is a carboxyl group, and the corresponding binding group BG3 is a carboxyl group.

That is, the polymer replica has, on its surface, a functional group of a kind corresponding to the kind of the functional group of the target substance at a position corresponding to the position of the functional group of the corresponding target substance. That is, the functional group information (specifically, the positional information and the qualitative information of the functional group) on the surface of the target substance is accurately copied.

As described above, the functional group information on the surface of the target substance is accurately copied to the polymer replica. Therefore, the polymer replica itself serves as a template in molecular imprinting for preparation of a molecular recognition material for the target substance. That is, the molecular recognition material for the target substance can be prepared without using the target substance itself, which is a biological substance, as a template. The polymer replica is a synthetic polymer material, so that the chemical stability and the physical stability are extremely excellent. Therefore, the polymer replica is much more useful as a template than the target substance, which is a biological substance. Furthermore, the polymer replica can be produced at low cost and can be reused as a template, so that the polymer replica is much more economical than the target substance, which is generally an expensive and rare biological substance, used as a template.

The component of the polymer replica and the method for producing the polymer replica will be described in detail in the following section "2. Method for Producing Polymer Replica of Target Substance".

[2. Method for Producing Polymer Replica of Target Substance]

Figure 3:
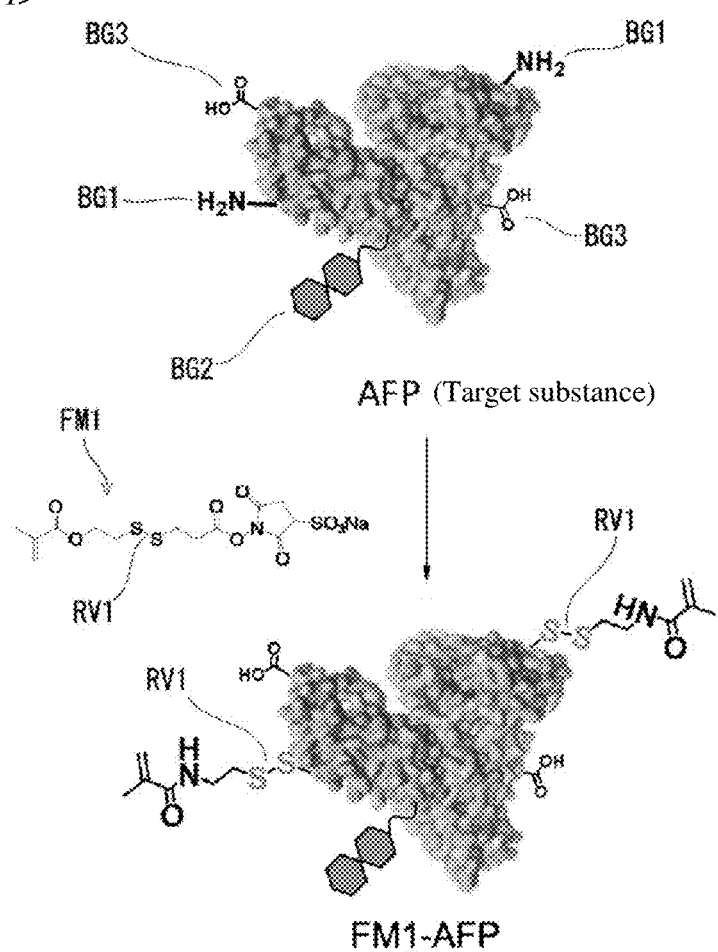
FIG. 3 schematically illustrates a step 1 in a method for producing a polymer replica of a target molecule, according to an embodiment of the present invention.
Figure 4:
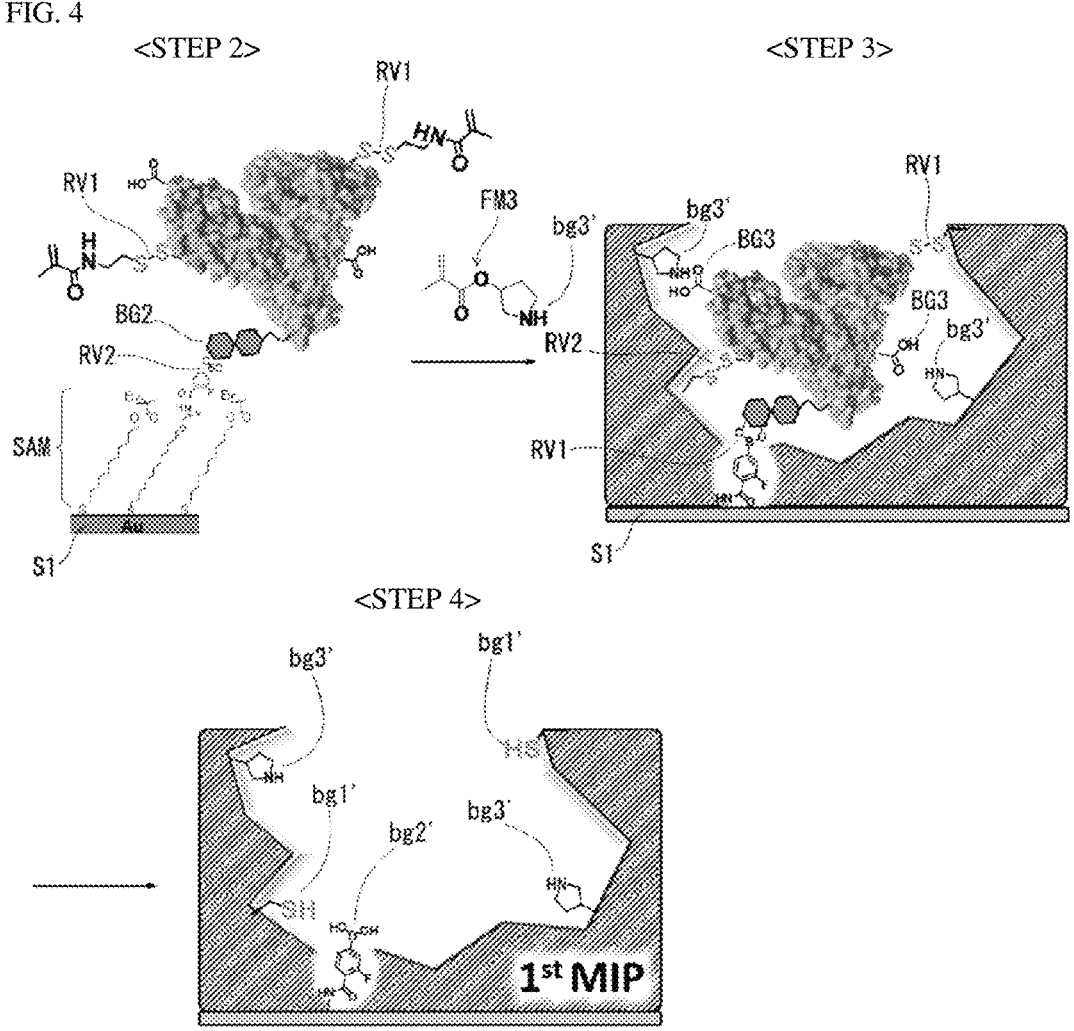
FIG. 4 schematically illustrates steps 2 to 4 in a method for producing a polymer replica of a target molecule, according to an embodiment of the present invention.
Figure 5:
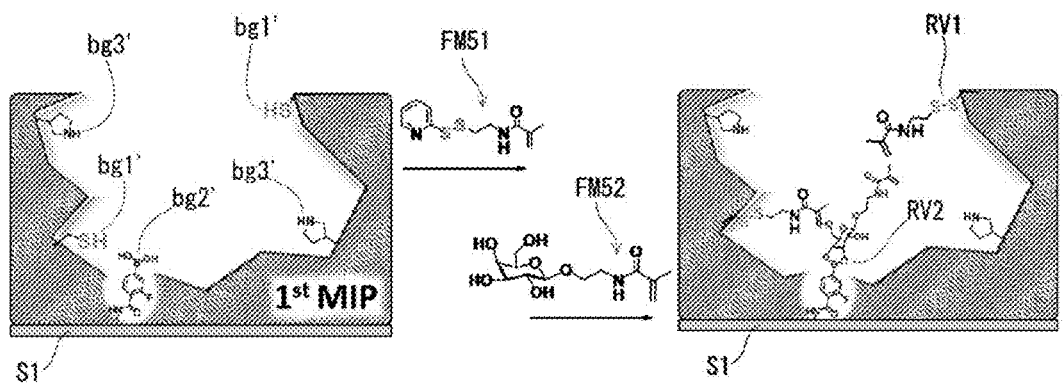
FIG. 5 schematically illustrates steps 5 to 7 in a method for producing a polymer replica of a target molecule, according to an embodiment of the present invention.
Figure 5:
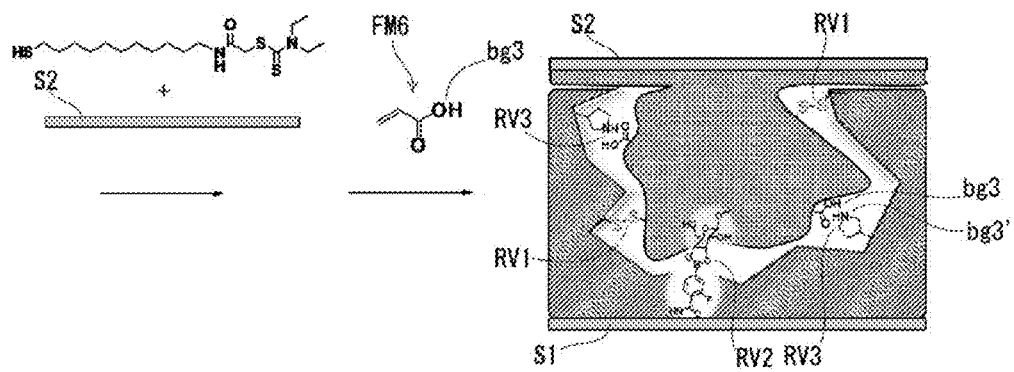
Figure 5:
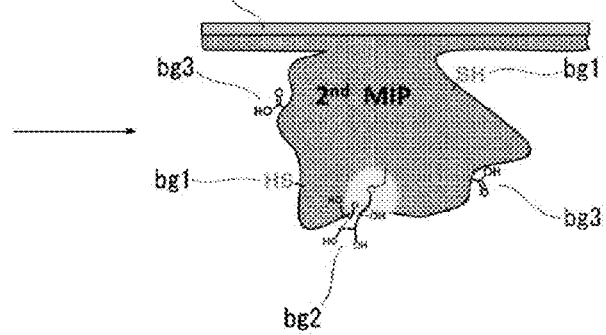

The method for producing a polymer replica according to the present invention will be described with reference to FIGS. 3 to 5. The method for producing a polymer replica according to the present invention includes the steps 1 to 4 of preparing a first molecularly imprinted polymer (1st MIP) using a target substance as a template, and the steps 5 to 7 of preparing a second molecularly imprinted polymer (2nd MIP), that is, a polymer replica portion using the first molecularly imprinted polymer as a template.

[Step 1: Introduction of Vinyl Group into Target Substance]

In the step 1, a functional monomer FM1 having a vinyl group and a reversible linking group RV1 is bonded to a target substance having a plurality of kinds of binding groups on its surface through at least a binding group BG1 among the plurality of kinds of binding groups. Through the step 1, the vinyl group is introduced into at least the binding group BG1 of the target substance through the reversible linking group RV1. In the illustrated aspect, a functional monomer FM1 having a vinyl group and a disulfide group (reversible linking group RV1) is introduced into a side chain amino group (binding group BG1) of a target substance, AFP.

The functional monomer FM1 has, for example, a specific structure as described below.

(I)

In the above formula, W represents a vinyl monomer group. The vinyl monomer group is not particularly limited as long as it can be copolymerized with another vinyl monomer for formation of a molecularly imprinted polymer, and examples the vinyl monomer group include a vinyl group, a methylvinyl group, a chlorovinyl group, (meth)acrylic acid ester groups, and methacrylic acid ester groups. Preferable examples of the vinyl monomer group include (meth)acrylic acid ester groups, and more preferable examples include methacrylic acid ester groups as shown in the drawings.

X and Z each independently represent a single bond or a linker group. Z is preferably a linker group particularly in the case that the polymer replica substrate of the target substance is obtained in which the binding group (for example, the binding group bg1) bonded to the position corresponding to the position of the binding group (for example, the binding group BG1) of the target substance is a different kind of binding group from the binding group BG1. In this case, in the method for producing a substrate sensor from a polymer replica substrate of a target substance described below, a space can be generated between the binding group bg1' and the position approached by the binding group BG1 of the target substance to be detected, and this space can easily ensure an arrangement space for the substance to be bonded to the binding group bg1' (specifically, the post-imprinting compound and/or the signal substance described in the step 14 described below).

Examples of the linker group include alkylene groups having 1 to 6, preferably 2 to 6 carbon atoms, an amino group (—NH—), an ether group (—O—), a carbonyl group (—C(=O)—), an ester group (—C(=O)—O— or —O—C(=O)—), an amide group (—C(=O)—NH— or —NH—C(=O)—), a sulfoxide group (—S(=O)—), a sulfonyl group (—S(=O)$_2$—), and groups in which two or more of the above-described groups are bonded. In the case that two or more of the above-described groups are bonded to form the linker group, the number of the bonded groups is preferably 5 or less or 4 or less, and more preferably 3 or less or 2. Preferable examples of the linker group include alkylene groups as shown in the drawings.

Y represents a reversible linking group. In the present invention, the term "reversible linking group" generally means a divalent or higher valent group in which the cleavage (break) and the bond are reversible, and the bond in the reversible linking portion may be a covalent bond or non-covalent bond. Specific examples of the reversible linking group include the groups in the first column of Table 2 described below. However, in the functional monomer FM1, the reversible linking group represented by Y means a group in which the bond in the reversible linking portion is a covalent bond, that is, a divalent or higher valent group in which the cleavage (break) of the covalent bond and the covalent bond are reversible. Specific examples of such a reversible linking group include the groups, among the groups in the first column of Table 2 described below, in which the bond in the reversible linking portion is a covalent bond. Such a reversible linking group is stable compared with a non-covalent bond such as a hydrogen bond, is stably maintained even during a polymerization reaction, and contributes to the formation of a specific recognition space, while relatively easily cleaved. Therefore, after the polymerization reaction, the template compound is easily removed. The reversible linking group can be cleaved by, for example, a reducing agent, heating at a relatively low temperature, hydrolysis under a relatively mild condition, or light irradiation. For example, carboxylic acid ester groups are cleaved more easily than an amide bond included in a protein, and can be selectively cleaved by hydrolysis under a relatively mild condition. Among carboxylic acid esters, o-nitrobenzyl ester groups can be selectively cleaved even by light irradiation.

In the present invention, reversible linking groups are generally described as a reversible linking group RV1, a reversible linking group RV2, a reversible linking group RV3, and so on. With respect to the reversible linking group RV1, the reversible linking group RV2, the reversible linking group RV3, and so on, the cleavage residues generated by the cleavage of the reversible linking groups are described as the binding group bg1 and the binding group bg1', the binding group bg2 and the binding group bg2', the binding group bg3 and the binding group bg3', and so on, respectively. In the present invention, a combination of a reversible linking group and cleavage residues (binding groups) generated by cleavage of the reversible linking group, and a bond in the reversible linking portion are, for example, as described below.

TABLE 2

| 1<br>Reversible linking group<br>(RV1, RV2, RV3 . . . ) | 2<br>Binding group<br>(bg1, bg2, bg3 . . . ) | 3<br>Binding group<br>(bg1', bg2', bg3' . . . ) | 4<br>Kind of bond in reversible<br>linking portion |
| --- | --- | --- | --- |
| Disulfide group | Thiol group<br>Pyridyl disulfide group | Thiol group<br>Pyridyl disulfide group | Covalent bond |
| Boronate-cis-diol ester group | Sugar group (cis-diol group) | Boronic acid group | Covalent bond |
| Imino-bonding group | Aldehyde group<br>Amino group | Amino group<br>Aldehyde group | Covalent bond |
| Carboxylic acid ester group | Carboxyl group<br>Hydroxyl group | Hydroxyl group<br>Carboxyl group | Covalent bond |
| Hydrogen bond and electrostatic interaction | Acidic group<br>(such as carboxyl group) | Basic group<br>(amino group, cyclic secondary amino group (such as pyrrolidyl group or piperidyl group), pyridyl group, imidazole group, guanidine group, or the like), hydroxyl group | Non-covalent bond |
| Intermolecular specific interaction | Antigenic determinant (epitope) | Antibody, paratope | Non-covalent bond |
| Hydrophobic interaction | Aromatic group<br>(phenyl group such as aminophenyl group, naphthyl group such as aminonaphthyl group, pyridyl group, or the like) | Aromatic group<br>(phenyl group such as aminophenyl group, naphthyl group such as aminonaphthyl group, pyridyl group, or the like) | Non-covalent bond |

$Q^1$ represents a binding group corresponding to the binding group BG1. As the binding group corresponding to the binding group BG1, a group capable of forming a covalent bond with the binding group BG1 can be appropriately determined by those skilled in the art according to the kind of the binding group BG1. Specific examples of the binding group corresponding to the binding group BG1 can be selected from the groups capable of forming a covalent bond with the binding group BG1 that are exemplified in the middle column of Table 1 described above. In the case that the binding group of the target substance is a carboxyl group, the binding group may be modified into a covalent binding group in advance by active esterification by N-hydroxysuccinimide, nitrophenol, pentafluorophenol, or the like. In the illustrated aspect, a carboxylic acid active ester group (active ester group by sodium N-hydroxysulfosuccinimide) is used as the binding group corresponding to the binding group BG1.

The reaction between the binding group BG1 of the target substance and the functional monomer FM1 can be carried out by a known method. In the case that the binding group of the target substance is an amino group, for example, if the binding group of the functional monomer FM1 is a carboxylic acid ester group, the target substance and the functional monomer FM1 may be mixed for reaction, and if the binding group of the functional monomer FM1 is a carboxylic acid, the target substance and the functional monomer FM1 may be reacted in the presence of a dehydration-condensation agent for formation of an amide bond.

[Step 2: Immobilization of Target Substance on Substrate]

In the step 2, the target substance is immobilized on a substrate S1. The target substance is immobilized on the substrate S1 through a reversible linking group RV2 by reacting a binding group, among the binding groups of the target substance, other than the binding group used for the introduction of the vinyl group in the step 1 (binding group BG2 in the illustrated example) on the substrate S1. The substrate S1 is surface-modified in advance by bonding a surface-modifying group, and the target substance can be immobilized on the substrate S1 by utilizing the binding property between the binding group at the terminal of the surface-modifying group and the binding group BG2 of the target substance. For example, it is preferable that a self-assembled monolayer (SAM) be formed on the substrate S1 in advance, and the target substance be immobilized by utilizing the binding property between the binding group at the SAM terminal (SAM surface) and the binding group BG2 of the target substance as shown in the drawings. The SAM is stable and uniform because it is chemically bonded to the substrate S1 and because the molecules are closely and regularly aligned on the substrate S1 due to the intermolecular force.

The material of the substrate S1 to be surface-modified is not particularly limited as long as the material reacts with a surface-modifying reagent having a surface-modifying group, and examples of the material include metals, glass, and resins. As the metal included in the substrate S1 for formation of the SAM, for example, gold is widely used, and silver, copper, platinum, palladium, and the like can also be used. In addition, a glass substrate or a Teflon (registered trademark) substrate on which a thin film of the above-described metal is formed can also be used as the metal substrate. Furthermore, a commercially available metal substrate may be used such as a metal substrate that is commercially available and suitable for a measurement method such as a surface plasmon resonance measurement method or a quartz crystal microbalance method described below. Examples of the resins include poly(meth)acrylates, polystyrene, ABSs (acrylonitrile-butadiene-styrene copolymers), polycarbonate, polyesters, polyethylene, polypropylene, nylons, polyurethanes, silicone resins, fluorine resins, methylpentene resins, phenol resins, melamine resins, epoxy resins, and vinyl chloride resins.

Examples of the surface-modifying reagent for formation of surface modification such as that of the SAM include straight-chain alkanes having 8 or more carbon atoms and having, at one terminal, a binding group to the surface of the substrate S1 (such as, in the case that the substrate S1 is a metal substrate, a thiol group or an acetic acid thioester group capable of binding to the surface of the metal substrate) and, at the other terminal, a binding group corresponding to the binding group BG2 of the target substance. Specific examples of the binding group corresponding to the binding group BG2 of the target substance at the other terminal can be selected from the groups exemplified in the middle column of Table 1. As the surface-modifying reagent for formation of surface modification such as that of the SAM, a straight-chain alkane may be further mixed having 8 or more carbon atoms and having, at one terminal, the binding group to the surface of the substrate S1 and, at the other terminal, a polymerization-initiating group. In this case, the polymerization-initiating group functions as a polymerization initiator in the copolymerization reaction in the step 3 described below. Hereinafter, a case in which a SAM is formed for surface modification of the surface of the substrate S1 will be described as a representative.

In the case that the target molecule is a glycoprotein, a sugar group is preferably used as the binding group BG2 for immobilization to the substrate S1 as shown in the drawings, and a boronic acid group is preferably immobilized on the substrate S1. In the case that the target molecule is a protein or a glycoprotein, the epitope of the target molecule is preferably used as the binding group BG2 for immobilization to the substrate S1, and the paratope for the epitope is preferably immobilized on the substrate S1. These cases are preferable because the orientations of a plurality of target molecules immobilized on the substrate S1 are aligned.

In the case of using a metal substrate as the substrate S1, a SAM can be formed on the metal substrate by a conventional method. For example, a SAM is formed by dissolving SAM-forming molecules in a solvent such as ethanol, and immersing a metal substrate in the resulting solution at room temperature for a predetermined time (for example, 30 minutes or more and about 48 hours or less) to bond each molecule to the surface of the metal substrate through a thioether bond, and to assemble the molecules closely while the molecules are oriented by intermolecular force. Alternatively, the SAM-forming molecule may be extended stepwise through the linker group exemplified in the step 1 described above. In this case, the binding group used for immobilization of the target protein is introduced into the final terminal, and in the case that a polymerization-initiating group is also provided as a SAM terminal group in addition to the binding group, the polymerization-initiating group is to be introduced into the final terminal in the same manner. Then, after removing the excess SAM-forming molecules by washing, the resulting product is to be dried.

In the case of using a glass substrate as the substrate S1, a SAM can be formed by introducing a reactive group such as an amino group onto the surface with a silane coupling agent such as 3-aminopropyltriethoxysilane (APTES).

After the formation of a SAM, the binding group BG2 of the target substance is reacted with the binding group at the SAM terminal to immobilize the target substance on the substrate S1. A reversible linking group RV2 is interposed between the SAM and the immobilized target substance. The reversible linking group RV2 allows the removal of the target substance from the first molecularly imprinted polymer in the step 4 described below. Specific examples of the reversible linking group RV2 can be selected from the groups in the first column of Table 2 described above.

The reversible linking group RV2 may be included in the linker group between the SAM and the target substance, or may be formed as a result of the reaction between the binding group at the SAM terminal and the binding group BG2 of the target substance. The reversible linking group RV2 is preferably formed as a result of the reaction between the binding group at the SAM terminal and the binding group BG2 of the target substance. Specifically, as shown in the drawings, a boronic acid group is introduced as the binding group at the SAM terminal and reacted with the sugar group as the binding group BG2 included in the target substance to form a boronate-cis-diol ester group as the reversible linking group RV2. Alternatively, a thiol group or an active thiol group is introduced at the terminal of the SAM and reacted with the thiol group derived from cysteine in the target substance or a thiol group introduced by a linker group-introducing reagent to form a disulfide bond as the reversible linking group RV2.

The reversible linking group RV2 interposed between the substrate S1 and the immobilized target substance may be the same as or different from the reversible linking group RV1 introduced together with the vinyl group in the step 1.

The reaction condition for the immobilization of the target substance can be appropriately selected by those skilled in the art according to the combination of the binding group on the substrate S1 and the binding group BG2 of the target substance. For example, in the case that the binding group at the SAM terminal is a boronic acid group and the binding group BG2 in the target substance is a sugar group, or in the case that the binding group at the SAM terminal is a pyridyl disulfide group and the binding group BG2 in the target substance is a thiol group, the reaction is so easy as to proceed by contact between the substrate S1 and the target substance in the solvent.

Alternatively, in the step 2, in the case that the target substance is immobilized on the substrate S1 by utilizing an intermolecular specific interaction, such as the case that the binding group at the SAM terminal is a paratope and the binding group BG2 in the target substance is an epitope, for example, the substrate S1 and the target substance are to be brought into contact with each other in a buffer solution in which the interaction is effective.

The fact that the target substance is immobilized can be confirmed by a method such as a surface plasmon resonance measurement method in the case of using, as the substrate S1, a metal substrate used for the surface plasmon resonance measurement method, or such as a quartz crystal microbalance method in the case of using, as the substrate S1, a metal substrate used for the quartz crystal microbalance method. After completion of the immobilization of the target substance, the substrate is washed to purify the desired immobilized target substance.

[Step 3: Molecular Imprinting (Synthesis of First Molecularly Imprinted Polymer, 1st MIP)]

In the step 3, molecular imprinting is performed, using the target substance immobilized in the step 2 as a template, by adding a vinyl monomer onto the substrate S1. Specifically, living radical polymerization proceeds by formation of a polymerization reaction system in which the vinyl group introduced into the target substance in the step 1, the vinyl monomer, and the target substance as a template coexist on the surface of the substrate S1. The vinyl monomer is copolymerized with the vinyl group introduced into the target substance in the step 1 to form a polymer matrix (first molecularly imprinted polymer) around the target substance.

The vinyl monomer to be added to the polymerization reaction system is not particularly limited as long as the vinyl monomer has a vinyl group structure copolymerizable with the vinyl group introduced into the target substance in the step 1 (that is, the vinyl monomer group of the functional monomer FM1), and can be appropriately selected by those skilled in the art. The first molecularly imprinted polymer synthesized in the step 3 is used as a template during the synthesis of the second molecularly imprinted polymer in the step 6 described below. Therefore, the vinyl monomer does not need to contain a biocompatible polymer. From the viewpoint of obtaining a property suitable for the template for the first imprinted polymer in the step 6 described below, the vinyl monomer is preferably water-soluble acrylamide because the hardness of such a polymer can be easily controlled. The rate of the number of moles of the acrylamide to the total amount of monomers is, for example, 50% or more, preferably 75% or more, and more preferably 90% or more.

The vinyl monomer may contain a functional monomer FM3. The functional monomer FM3 has, for example, a specific structure as described below.

$$W-X-Q^3 \qquad (II)$$

In the above-described formula, W represents a vinyl monomer group, and X represents a single bond or a linker group. W and X are selected from the groups exemplified as W and the groups exemplified as X in the functional monomer FM1 described in the step 1, respectively.

$Q^3$ represents a binding group bg3' corresponding to the binding group BG3 included in the target substance. As the binding group bg3' corresponding to the binding group BG3, a group capable of forming a non-covalent bond (reversible linking group RV3) with the binding group BG3 can be appropriately determined by those skilled in the art preferably according to the kind of the binding group BG3. Specific examples of the binding group bg3' corresponding to the binding group BG3 can be selected from the non-covalent binding groups exemplified in the middle column of Table 1 (or in the third column of Table 2) described above. In the illustrated aspect, the binding group BG3 is assumed to be a side chain acidic group (preferably a carboxyl group) of the protein moiety, and as the binding group bg3' corresponding to the binding group BG3, a basic group is used. The basic group can be selected from an amino group, cyclic secondary amino groups (such as a pyrrolidyl group and a piperidyl group), a pyridyl group, an imidazole group, and a guanidine group. Preferable examples of the basic group include secondary amino groups (such as a pyrrolidyl group and a piperidyl group), and a pyrrolidyl group is more preferable. The vinyl monomer containing such a functional monomer FM3 is copolymerized to obtain a first molecularly imprinted polymer in which the binding group BG3 in the target substance and the binding group bg3' derived from the functional monomer FM3 can form a hydrogen bond as the reversible linking group RV3.

In the polymerization reaction system, a crosslinking agent may be used in combination with the vinyl monomer. Examples of the crosslinking agent include compounds in which two or more vinyl monomer groups are bonded through a linker group. Specific examples of the crosslinking agent include compounds represented by the general formula W—X—W (in the formula, W represents a vinyl monomer group, and X represents a linker group). The vinyl monomer group W and the linker group X included in the crosslinking agent are the same as described above. More specific examples of the crosslinking agent include low molecular weight crosslinking agents such as N,N'-methylenebisacrylamide and ethylene glycol dimethacrylate. The crosslinking agent is used at a rate of the number of moles of the crosslinking agent to the total number of moles of the vinyl monomer and the crosslinking agent of, for example, 5% or more, preferably 10% or more, more preferably 15% or more, and still more preferably 18% or more from the viewpoint of further accurate inheritance of the surface information of the template by the first imprinted polymer obtained by the crosslinking and/or the viewpoint of the appropriate strength of the first imprinted polymer as a template in the step 6 described below. From the viewpoint of controlling the hardness of the first imprinted polymer to be not too high so that after used as a template for molecular imprinting in the step 6 described below, the first imprinted polymer can be easily removed in the step 7, the rate of the number of moles of the crosslinking agent to the total number of moles of the vinyl monomer and the crosslinking agent is, for example, 30% or less, preferably 25% or less, and more preferably 22% or less. That is, the specific range of the rate of the number of moles of the crosslinking agent to the total number of moles of the vinyl monomer and the crosslinking agent is, for example, 5 to 30%, 5 to 25%, 5 to 22%, 10 to 30%, 10 to 25%, 10 to 22%, 18 to 30%, 18 to 25%, or 18 to 22%.

The polymerization reaction system preferably further includes, as a polymerization catalyst, a transition metal or a transition metal complex including a transition metal compound and a ligand, and more preferably further includes a reducing agent to be used. Examples of the transition metal or the transition metal compound include metallic copper and copper compounds, and examples of the copper compound include a chloride, a bromide, an iodide, a cyanide, an oxide, a hydroxide, an acetate, a sulfate, and a nitrate, and a bromide is preferable. The ligand is preferably a multidentate amine, and specific examples of the ligand include bidentate to hexadentate ligands. Among the ligands, bidentate ligands are preferable, 2,2-bipyridyl, 4,4'-di-(5-nonyl)-2,2'-bipyridyl, N-(n-propyl)pyridylmethaneimine, N-(n-octyl)pyridylmethaneimine, and the like are more preferable, and 2,2-bipyridyl is still more preferable. Examples of the reducing agent include alcohols, aldehydes, phenols, and organic acid compounds, and organic acid compounds are preferable. Examples of the organic compound include citric acid, oxalic acid, ascorbic acid, ascorbic acid salts, and ascorbic acid esters. Among the organic compounds, ascorbic acid, ascorbic acid salts, and ascorbic acid esters are preferable, and ascorbic acid is more preferable.

The copolymerization condition in the step 3 is appropriately determined by those skilled in the art. For example, a monomer such as acrylamide is water-soluble, and therefore in the presence of an aqueous solvent, at least, a vinyl monomer is added to a substrate on which the target substance is immobilized, and a polymerization initiator is used (polymerization-initiating group bonded to the SAM terminal of the substrate S1 may be used) to initiate polymerization. The polymerization temperature may be room temperature, or may be about 0° C. or more and 120° C. or less, and the polymerization time can be about 10 minutes or more and 50 hours or less. After the copolymerization reaction, the substrate is preferably washed with the used solvent or the like to remove the excess reagent.

[Step 4: Removal of Target Substance]

In the step 4, the reversible linking group RV1 and the reversible linking group RV2 are cleaved and the target substance is removed. As a result, a negative first molecularly imprinted polymer is obtained that includes a recess generated using the target substance as a template and includes a binding group bg1' and a binding group bg2' as cleavage residues on the surface of the recess. In the illustrated aspect, the reversible linking group RV3 is also cleaved in addition to the reversible linking group RV1 and the reversible linking group RV2 to obtain a first molecularly imprinted polymer including also the binding group bg3' in addition to the binding group bg1' and the binding group bg2'. The binding group bg1', the binding group bg2', and the binding group bg3' are a cleavage residue of the reversible linking group RV1, a cleavage residue of the reversible linking group RV2, and a cleavage residue of the reversible linking group RV3, respectively, and specific examples thereof are listed in the third column of Table 2.

The way of cleavage of the reversible linking group can be appropriately determined by those skilled in the art according to the kind of each reversible linking group. For example, in the case that the reversible linking group RV1, the reversible linking group RV2, and the reversible linking group RV3 are a disulfide bond, a boronate-cis-diol ester group, and a hydrogen bond respectively as illustrated in the drawings, the reversible linking groups are to be subjected to a condition for cleavage of the disulfide bond and the boronate-cis-diol ester group. More specifically, the reversible linking groups are to be subjected to a pH at which boronate-cis-diol ester is hydrolyzable by bringing a reducing agent capable of cleaving a disulfide bond into contact with the substrate on which the first molecularly imprinted polymer obtained in the step 3 is formed in a suitable solvent at room temperature. Examples of the reducing agent include tris (2-carboxyethylphosphine) (TCEP), dithiothreitol (DTT), and tributylphosphine (TBP). As a result, the covalent binding reversible linking group RV1 and reversible linking group RV2 are cleaved, and the hydrogen-bonding reversible linking group RV3 is also cleaved. After the cleavage of the reversible linking group, the substrate on which the first molecularly imprinted polymer is formed is preferably washed.

In this way, the first molecularly imprinted polymer is obtained. The first molecularly imprinted polymer is used as a template for further molecular imprinting in the step described below. Therefore, the first imprinted polymer preferably has a polymer composition different from that of a molecularly imprinted polymer used as a normal sensor substrate. That is, the first imprinted polymer does not need to have a property, such as biocompatibility, required for analysis, and is to satisfy a mechanical property as a template. The first imprinted polymer more preferably includes polyacrylamide as a main component, and still more preferably includes only polyacrylamide, except for the monomer-derived moieties giving the binding group bg1', the binding group bg2', and the binding group bg3'.

[Step 5: Introduction of Vinyl Group into First Molecularly Imprinted Polymer]

In the step 5, a functional monomer FM51 and a functional monomer FM52 each having a vinyl group are respectively bonded through at least the binding group bg1' and the binding group bg2' on the surface of the recess of the first molecularly imprinted polymer. As will be described below, the functional monomer FM51 and the functional monomer FM52 have a group capable of reacting with the binding group bg1' to form a reversible linking group RV1, and a group capable of reacting with the binding group bg2' to form a reversible linking group RV2, respectively. Therefore, in the step 4, a vinyl group is introduced into at least the binding group bg1' and the binding group bg2' on the surface of the recess of the first molecularly imprinted polymer through the reversible linking group RV1 and the reversible linking group RV2, respectively.

The functional monomer FM51 has, for example, a specific structure as described below.

W—X-Q$^{51}$ (III)

In the above-described formula (III), W represents a vinyl monomer group, and X represents a single bond or a linker group. W and X are selected from the groups exemplified as W and the groups exemplified as X in the functional monomer FM1 described in the step 1, respectively.

Q$^{51}$ represents a binding group corresponding to the binding group bg1'. As the binding group corresponding to the binding group bg1', a group capable of reacting with the binding group bg1' to form a reversible linking group RV1 can be appropriately determined by those skilled in the art according to the kind of the binding group bg1'. Specific examples of the binding group corresponding to the binding group bg1' include the covalent binding groups in the second column of Table 2 described above.

The functional monomer FM52 has, for example, a specific structure as described below.

W—X-Q$^{52}$ (IV)

In the above-described formula (IV), W represents a vinyl monomer group, and X represents a single bond or a linker group. W and X are selected from the groups exemplified as W and the groups exemplified as X in the functional monomer FM1 described in the step 1, respectively. The vinyl monomer group W and the single bond or linker group X in the functional monomer FM52 may be the same as or different from the vinyl monomer group W and the single bond or linker group X in the functional monomer FM51 described above.

Q$^{52}$ represents a binding group corresponding to the binding group bg2'. As the binding group corresponding to the binding group bg2', a group capable of reacting with the binding group bg2' to form a reversible linking group RV2 can be appropriately determined by those skilled in the art according to the kind of the binding group bg2'. Specific examples of the binding group corresponding to the binding group bg2' include the covalent binding groups in the second column of Table 2 described above. In the present invention, the binding group Q$^{51}$ in the functional monomer FM51 is usually different from the binding group Q$^{52}$ in the functional monomer FM52.

The conditions for the reaction of the functional monomer FM51 and the reaction of the functional monomer FM52 can be appropriately selected by those skilled in the art according to the combination of the binding group bg1' and the binding group bg2'. The order of bonding the functional monomer FM51 and the functional monomer FM52 is not particularly limited, and can be appropriately determined by those skilled in the art considering whether the conditions for the reaction with the binding group bg1' and the conditions for the reaction with the binding group bg2' (such as the temperature, the time, the pH, and the kind of the solvent) are the same or different, and considering the stability of the reversible linking group RV2 under the conditions for the reaction with the binding group bg1' and the stability of the reversible linking group RV1 under the conditions for the reaction with the binding group bg2'. For example, the functional monomer FM51 and the functional monomer FM52 may be each reacted in the same reaction system to each react the reversible linking group RV1 and the reversible linking group RV2 at the same time, or the functional monomer FM51 may be reacted to form a reversible linking group RV1 and then the functional monomer FM52 may be reacted to form a reversible linking group RV2, or the functional monomer FM52 may be reacted to form a reversible linking group RV2 and then the functional monomer FM51 may be reacted to form a reversible linking group RV1. For example, in the case that the functional monomer FM51 has a pyridyl sulfide group to the thiol group as the binding group bg1' and the functional monomer FM52 has a sugar group to the boronic acid group as the binding group bg2' as shown in the drawings, both the reactions are easy, and the following procedure can be performed. First, the functional monomer FM51 is added to carry out a reaction in a suitable solvent, washing is performed, then the functional monomer FM52 is added to carry out a reaction in another suitable solvent, and then washing is performed.

[Step 6: Molecular Imprinting (Synthesis of Second Molecularly Imprinted Polymer, 2nd MIP)]

In the step 6, molecular imprinting is performed using the first molecularly imprinted polymer as a template by adding a vinyl monomer onto the first molecularly imprinted polymer. A polymerization reaction system is formed in which the vinyl group introduced into the first molecularly imprinted polymer in the step 5, the vinyl monomer, and the first molecularly imprinted polymer as a template coexist. The vinyl monomer is copolymerized with the vinyl group introduced in the step 5 to form a polymer matrix (second molecularly imprinted polymer) around the recess of the first molecularly imprinted polymer.

In the case of producing a substrate-integrated polymer replica as shown in FIG. 2(a), the first molecularly imprinted polymer is laminated with a substrate S2 through the vinyl monomer to form a polymerization reaction system between the substrate S2 and the first molecularly imprinted polymer. In the case of producing a particle-shaped polymer replica as shown in FIG. 2(b), a polymerization reaction system is formed in the recess of the first molecularly imprinted polymer.

The material of the substrate S2 is not particularly limited, and is, for example, a metal, glass, or a resin. Examples of the material of the metal substrate include gold, silver, copper, platinum, and palladium, and gold is preferable. The metal substrate may be a glass substrate or a Teflon (registered trademark) substrate on which a thin film of the above-described metal is formed. Examples of the resin include poly(meth)acrylates, polystyrene, ABSs (acrylonitrile-butadiene-styrene copolymers), polycarbonate, polyesters, polyethylene, polypropylene, nylons, polyurethanes, silicone resins, fluorine resins, methylpentene resins, phenol resins, melamine resins, epoxy resins, and vinyl chloride resins. In the case that the substrate S1 is a metal substrate (that is not laminated with a glass substrate), the substrate S2 may be any of the above-described substrates, but from the viewpoint of facilitating the step 7 described below, a metal substrate (that is not laminated with a glass substrate) is preferable. In the case that the substrate S1 is a glass substrate or a glass substrate having a metal thin film, the substrate S2 is a metal substrate (that is not laminated with a glass substrate) from the viewpoint of facilitating the step 7 described below.

The substrate S2 is preferably surface-modified with an iniferter having a polymerization-initiating group at the terminal. The polymerization-initiating group in the surface modification on the substrate S2 is to be different from the polymerization-initiating group in the substrate S1. The iniferter forming the surface modification is stable and uniform because it is chemically bonded to the substrate S2 and because the molecules are closely and regularly aligned on the substrate S2 due to the intermolecular force.

The iniferter that can be used in the present invention is not particularly limited as long as the iniferter is a compound having a binding group to the substrate S2 and having a polymerization-initiating group. The general formula of the preferable iniferter is shown below.

[Chem. 1]

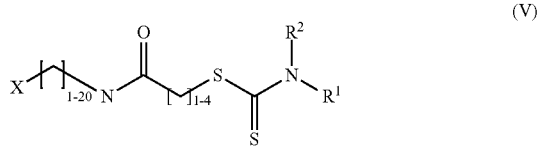

(V)

The iniferter represented by the above-described formula (V) has a binding group X to the substrate S2, a linker group for self-assembly (alkylene group having 1 to 20 carbon atoms), and a dithiocarbamate-based polymerization-initiating group (a free radical (—NR$^1$R$^2$) through a thiocarbonylthio group (S=C(—S—)—).

The binding group X can be appropriately determined depending on the material of the substrate S2. Examples of the binding group X include a thiol group and an acetic acid thioester group, and a thiol group is preferable. The iniferter molecules immobilized by the binding group X are closely and regularly aligned by the van der Waals force by the alkylene group having 1 to 20 carbon atoms to form a stable SAM film. From this point of view, the alkylene group having 1 to 20 carbon atoms preferably has 5 to 20 carbon atoms, and more preferably 10 to 20 carbon atoms. R$^1$ and R$^2$ in the free radical (—NR$^1$R$^2$) may be the same or different. For example, R$^1$ and R$^2$ may be selected from alkyl groups, cycloalkyl groups, aryl groups, allenyl groups, and heterocyclic groups, and preferably from alkyl groups. R$^1$ and R$^2$, together with the nitrogen to which they are bonded, may form a heterocycle. In some cases, R$^1$ and R$^2$ may be substituted with a phosphate, a phosphonate, a sulfonate, an ester, a halogen, a nitrile, an amide, or a hydroxy group. In some cases, R$^1$ and R$^2$ may be substituted with one or more catenary heteroatoms such as oxygen, nitrogen, and sulfur. R$^1$ and R$^2$ are preferably an alkyl group having 1 to 6 carbon atoms, and more preferably 2 to 4 carbon atoms, and an ethyl group is preferable.

The vinyl monomer to be added to the polymerization reaction system is not particularly limited as long as the vinyl monomer has a vinyl group copolymerizable with the vinyl group introduced into the first molecularly imprinted polymer in the step 5 (that is, the vinyl monomer group of the functional monomer FM51 and the vinyl monomer group of the functional monomer FM52), and can be appropriately selected by those skilled in the art.

Preferable examples of the vinyl monomer include biocompatible monomers. In the case of producing a substrate-integrated polymer replica as shown in FIG. 2(a), a biocompatible monomer is preferably used as the vinyl monomer from the viewpoint of suppressing non-specific adsorption of the monomer added when the polymer replica is used for post-molecular imprinting in the step 5 described below and for molecular imprinting in the step 6 (the functional monomers FM111, FM112, and FM6 described below). The term "biocompatible monomer" refers to a monomer capable of forming a biocompatible polymer. The biocompatible polymer is preferably a hydrophilic polymer, and more specifically a zwitterionic polymer. The zwitterionic monomer capable of forming a zwitterionic polymer includes, in one molecule, both an anionic group derived from an acidic functional group (such as a phosphate group, a sulfate group, or a carboxyl group) and a cationic group derived from a basic functional group (such as a primary amino group, a secondary amino group, a tertiary amino group, or a quaternary ammonium group). Examples of the zwitterionic monomer include phosphobetaines, sulfobetaines, and carboxybetaines, and phosphobetaines are more preferable.

Examples of the sulfobetaines include N,N-dimethyl-N-(3-sulfopropyl)-3'-methacryloylaminopropanaminium inner salt (SPB) and N,N-dimethyl-N-(4-sulfobutyl)-3'-methacryloylaminopropanaminium inner salt (SBB). Examples of the carboxybetaines include N,N-dimethyl-N-(1-carboxymethyl)-2'-methacryloyloxyethanaminium inner salt (CMB) and N,N-dimethyl-N-(2-carboxyethyl)-2'-methacryloyloxyethanaminium inner salt (CEB). Examples of the phosphobetaines include molecules having a phosphorylcholine group as the side chain, and 2-methacryloyloxyethyl phosphorylcholine (MPC) is more preferable.

The rate of the number of moles of the biocompatible monomer to the total amount of monomers is, for example, 50% or more, preferably 75% or more, more preferably 90% or more, and still more preferably 95% or more.

The vinyl monomer may contain a functional monomer FM6. The functional monomer FM6 has, for example, a specific structure as described below.

W—X-Q$^6$ (VI)

In the above-described formula (VI), W represents a vinyl monomer group, and X represents a single bond or a linker group. W and X are selected from the groups exemplified as W and the groups exemplified as X in the functional monomer FM1 described in the step 1, respectively.

Q$^6$ represents a binding group bg3 corresponding to the binding group bg3'. As the binding group bg3 corresponding to the binding group bg3', a group capable of forming a non-covalent bond (reversible linking group RV3) with the binding group bg3' can be appropriately determined by those skilled in the art preferably according to the kind of the binding group bg3'. Specific examples of the binding group bg3 corresponding to the binding group bg3' can be selected from the non-covalent binding groups exemplified in the second column of Table 2 described above. In the illustrated aspect, the binding group bg3' is assumed to be a basic group, and as the binding group bg3 corresponding to the binding group bg3', a carboxyl group is used. The vinyl monomer containing such a functional monomer FM6 is copolymerized to obtain a second molecularly imprinted polymer in which the binding group bg3' in the first molecularly imprinted polymer as a template and the binding group bg3 derived from the functional monomer FM6 can form a hydrogen bond as the reversible linking group RV3.

In the polymerization reaction system, a crosslinking agent may be used in combination with the vinyl monomer. Examples of the crosslinking agent include compounds in which two or more vinyl monomer groups are bonded through a linker group. Specific examples of the crosslinking agent include compounds represented by the general formula W—X—W (in the formula, W represents a vinyl monomer group, and X represents a linker group). The vinyl monomer group W and the linker group X included in the crosslinking agent are the same as described above. More specific examples of the crosslinking agent include low molecular weight crosslinking agents such as N,N'-methylenebisacrylamide and ethylene glycol dimethacrylate. The crosslinking agent is used at a rate of the number of moles of the crosslinking agent to the total number of moles of the vinyl monomer and the crosslinking agent of, for example, 5% or more, preferably 10% or more, more preferably 15% or more, and still more preferably 18% or more from the viewpoint of the appropriate strength of the second imprinted polymer obtained by the crosslinking and the viewpoint of further accurate inheritance, by the second imprinted polymer, of the surface information of the first imprinted polymer as a template. In the case of the substrate-integrated second imprinted polymer as shown in FIG. 2(a), the rate of the number of moles of the crosslinking agent to the total number of moles of the vinyl monomer and the crosslinking agent is, for example, 30% or less, preferably 25% or less, and more preferably 22% or less from the viewpoint of, for example, controlling the hardness of the second imprinted polymer to be not too high so that after used as a template for molecular imprinting in the step 12 described below, the second imprinted polymer can be easily removed by separating the substrates in the step 13. That is, the specific range of the rate of the number of moles of the crosslinking agent to the total number of moles of the vinyl monomer and the crosslinking agent is, for example, 5 to 30%, 5 to 25%, 5 to 22%, 10 to 30%, 10 to 25%, 10 to 22%, 18 to 30%, 18 to 25%, or 18 to 22%.

The polymerization reaction system preferably further includes, as a polymerization catalyst, a transition metal or a transition metal complex including a transition metal compound and a ligand, and more preferably further includes a reducing agent to be used. As the transition metal complex and the reducing agent, those described in the step 3 can be used.

The copolymerization condition in the step 6 is appropriately determined by those skilled in the art. For example, the biocompatible polymer is water-soluble, and therefore in the presence of an aqueous solvent, a vinyl monomer is added to the first molecularly imprinted polymer on the substrate S1, and a polymerization initiator is used to initiate polymerization. In the case that the polymerization initiator is a photopolymerizable initiator, the reaction is initiated under a light irradiation condition.

In the case of producing a substrate-integrated polymer replica as shown in FIG. 2(a), a reaction solution is filled between the surface of the first molecularly imprinted polymer and the substrate S2 laminated thereto. In the case that the surface of the substrate S2 is modified with an iniferter, the iniferter may be used as a polymerization initiator. In the case of producing a particle-shaped polymer replica as shown in FIG. 2(b), the amount of the reaction solution is adjusted so that the layer of the reaction solution on the first molecularly imprinted polymer is as thin as possible. As a result, a second molecularly imprinted polymer is obtained in a state of being independent from each recess of the first molecularly imprinted polymer (state of being a particle). Furthermore, by putting a polymerization initiator only in the recess of the first molecularly imprinted polymer before forming the polymerization reaction system, a second molecularly imprinted polymer in a state of being independent can be further easily obtained.

The polymerization temperature may be 0° C. or more and 120° C. or less, and preferably room temperature (5° C. or more and 35° C. or less, preferably 10° C. or more and 30° C. or less), and the polymerization time can be about 10 minutes or more and 50 hours or less. After the copolymerization reaction, the second molecularly imprinted polymer is preferably washed with the used solvent or the like to remove the excess reagent.

[Step 7: Removal of First Molecularly Imprinted Polymer]

In the step 7, the reversible linking group RV1 and the reversible linking group RV2 are cleaved and the first molecularly imprinted polymer is removed. As a result, a second molecularly imprinted polymer is obtained. In the case that the substrate S2 is used in the step 6, a positive second molecularly imprinted polymer as shown in FIG. 2(a) is obtained that includes a protrusion generated using the first molecularly imprinted polymer as a template and includes a binding group bg1 and a binding group bg2 as cleavage residues on the surface of the protrusion. In the case that the substrate S2 is not used in the step 6, a polymer replica as shown in FIG. 2(b) is obtained that has a particle shape obtained by using the first molecularly imprinted polymer as a template and includes a binding group bg1 and a binding group bg2 as cleavage residues on the surface.

In the illustrated aspect, the reversible linking group RV3 is also cleaved in addition to the reversible linking group RV1 and the reversible linking group RV2 to obtain a second molecularly imprinted polymer including also the binding group bg3 in addition to the binding group bg1 and the binding group bg2. The binding group bg1, the binding group bg2, and the binding group bg3 are a cleavage residue of the reversible linking group RV1, a cleavage residue of the reversible linking group RV2, and a cleavage residue of the reversible linking group RV3, respectively, and specific examples thereof are listed in the second column of Table 2.

The way of cleavage of the reversible linking group can be appropriately determined by those skilled in the art according to the kind of each reversible linking group. For example, in the case that the reversible linking group RV1, the reversible linking group RV2, and the reversible linking group RV3 are a disulfide bond, a boronate-cis-diol ester group, and a hydrogen bond respectively as illustrated in the drawings, the reversible linking groups are to be subjected to a condition for reduction of the disulfide bond and/or the boronate-cis-diol ester group. More specifically, the composite of the substrate S1, the first molecularly imprinted polymer on the substrate S1, and the second molecularly imprinted polymer obtained in the step 6 are to be immersed in a liquid containing a reducing agent at room temperature in an appropriate solvent. Examples of the reducing agent include tris (2-carboxyethylphosphine) (TCEP), dithiothreitol (DTT), and tributylphosphine (TBP). As a result, the covalent binding reversible linking group RV1 and reversible linking group RV2 are cleaved, and the hydrogen-bonding reversible linking group RV3 is also cleaved.

After the reduction reaction, the second molecularly imprinted polymer is taken out from the substrate S1 (and the first molecularly imprinted polymer on the substrate S1). In the case of producing a substrate-integrated polymer replica as shown in FIG. 2(a), it is preferable to separate the substrate S1 (and the first molecularly imprinted polymer on the substrate S1) and the substrate S2 (and the second molecularly imprinted polymer on the substrate S2) from the viewpoint of taking out the second molecularly imprinted polymer easily. In the case of producing a particle-shaped polymer replica as shown in FIG. 2(b), the second molecularly imprinted polymer can be further easily taken out by forming the first molecularly imprinted polymer or the second molecularly imprinted polymer that includes silica gel instead of a resin. For example, in the case that the first molecularly imprinted polymer includes silica gel, the second molecularly imprinted polymer can be further easily taken out by dissolving the first molecularly imprinted polymer.

In this way, the polymer replica of the target substance described in [1. Polymer Replica of Target Substance] is obtained.

[3. Method for Producing Substrate Sensor]

Figure 2:
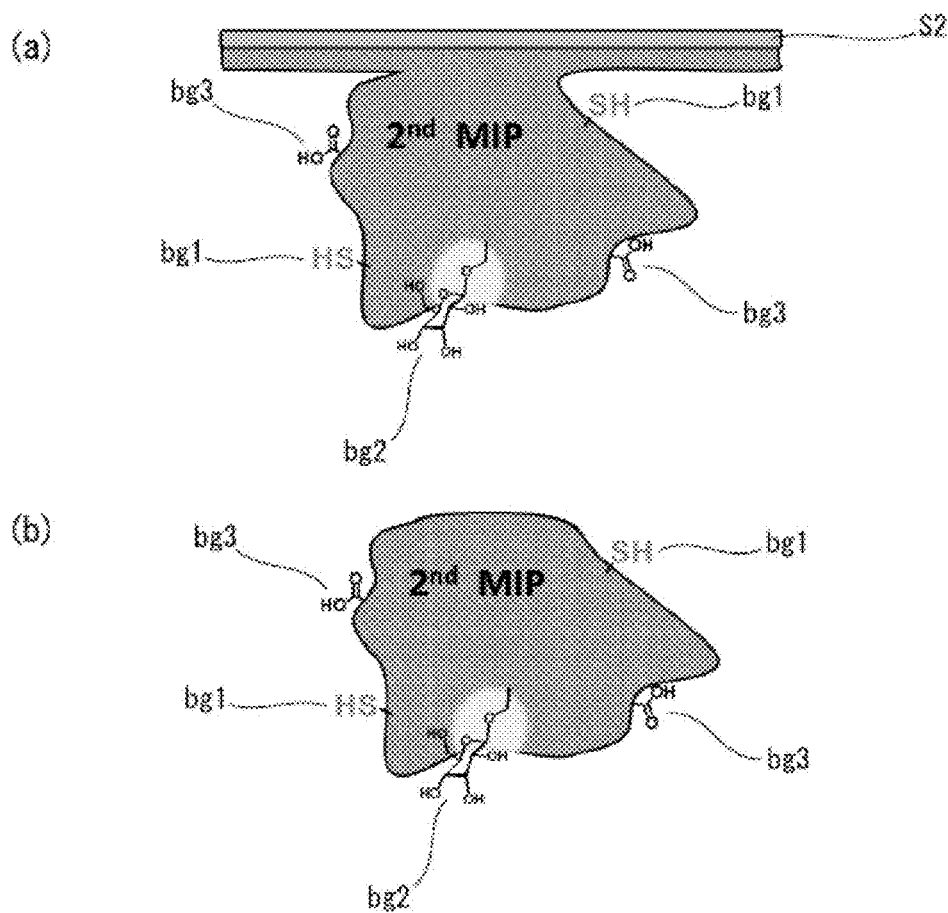
FIG. 2 schematically illustrates a polymer replica of a target molecule according to embodiments of the present invention. (a) Second molecularly imprinted polymer ($2^{nd}$ MIP) shown with substrate (S2). (b) Second molecularly imprinted polymer ($2^{nd}$ MIP).
Figure 6:
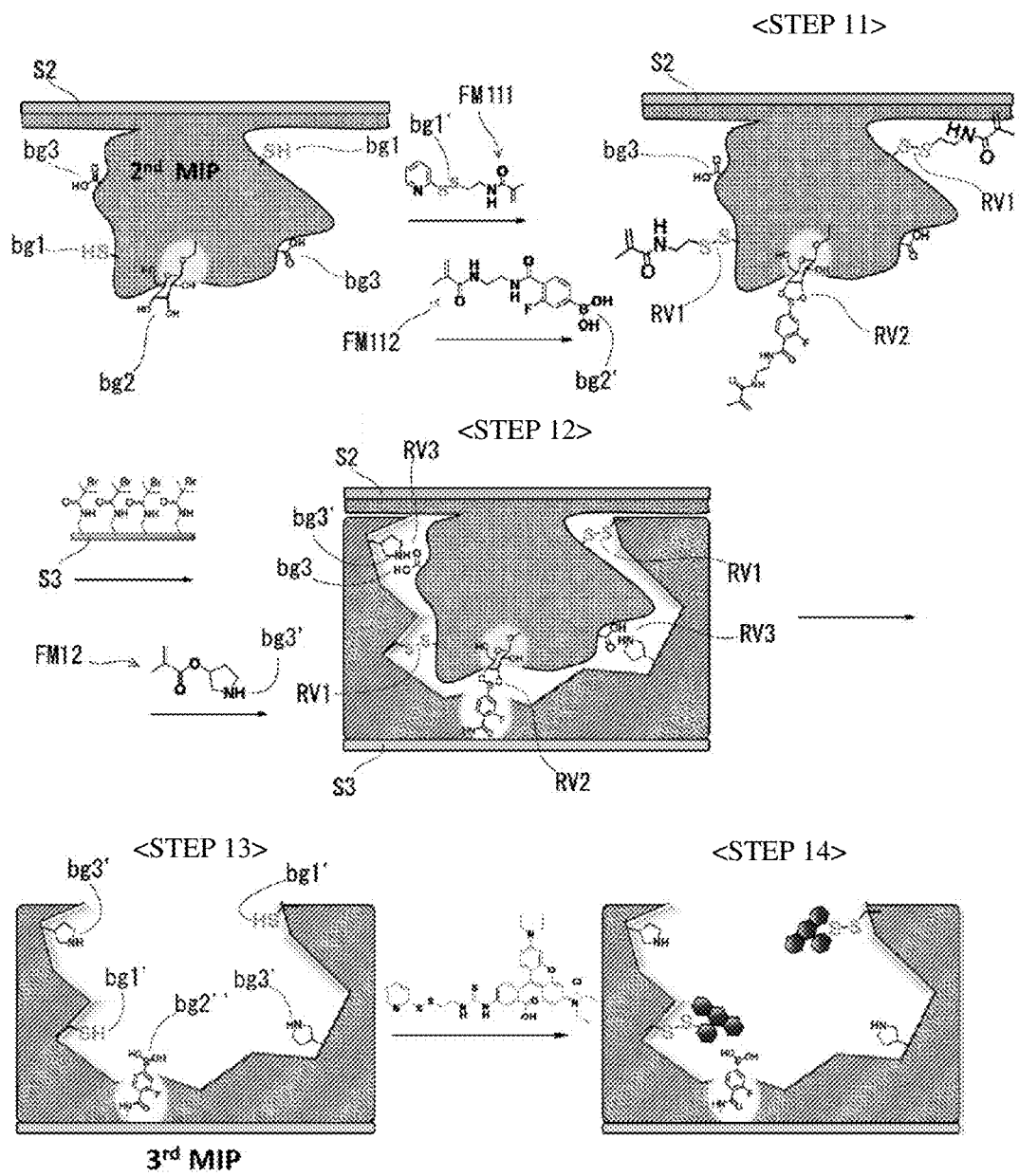
FIG. 6 schematically illustrates a method for producing a substrate sensor, according to an embodiment of the present invention.

The method for producing a substrate sensor according to the present invention will be described with reference to FIG. 6. The method for producing a substrate sensor according to the present invention includes the steps 11 to 13 of preparing a third molecularly imprinted polymer (3rd MIP) using the polymer replica of the target substance (substrate-integrated polymer replica as shown in FIG. 2(*a*)) as a template and the step 14 of bonding a post-imprinting compound and/or a signal substance to the third molecularly imprinted polymer.

[Step 11: Introduction of Vinyl Group into Second Molecularly Imprinted Polymer]

In the step 11, a functional monomer FM111 and a functional monomer FM112 each having a vinyl group are respectively bonded through at least the binding group bg1 and the binding group bg2 on the surface of the protrusion on the polymer replica substrate (protrusion-shaped polymer replica portion) of the target substance. As will be described below, the functional monomer FM111 and the functional monomer FM112 have a group capable of reacting with the binding group bg1 to form a reversible linking group RV1, and a group capable of reacting with the binding group bg2 to form a reversible linking group RV2, respectively. Therefore, in the step 11, a vinyl group is introduced into at least the binding group bg1 and the binding group bg2 on the surface of the protrusion of the second molecularly imprinted polymer through the reversible linking group RV1 and the reversible linking group RV2, respectively.

The functional monomer FM111 is the same as the functional monomer FM51 used in the above-described step 4 except that $Q^{51}$ in the above-described formula (III) is a binding group bg1' corresponding to the binding group bg1. The functional monomer FM112 is the same as the functional monomer FM52 used in the above-described step 4 except that $Q^{52}$ in the above-described formula (III) is a binding group bg2' corresponding to the binding group bg2. As the binding group bg1' corresponding to the binding group bg1, a group capable of reacting with the binding group bg1 to form a reversible linking group RV1 can be appropriately determined by those skilled in the art according to the kind of the binding group bg1. Specific examples of the binding group bg1' corresponding to the binding group bg1 include the covalent binding groups in the third column of Table 2 described above. As the binding group bg2' corresponding to the binding group bg2, a group capable of reacting with the binding group bg2 to form a reversible linking group RV1 can be appropriately determined by those skilled in the art according to the kind of the binding group bg2. Specific examples of the binding group bg2' corresponding to the binding group bg2 include the covalent binding groups in the third column of Table 2 described above. The reaction conditions and the like of the functional monomer FM111 and the functional monomer FM112 are the same as those in the above-described step 4.

[Step 12: Molecular Imprinting (Synthesis of Third Molecularly Imprinted Polymer, 3rd MIP)]

In the step 12, molecular imprinting is performed using the second molecularly imprinted polymer as a template in a state of adding a vinyl monomer onto the second molecularly imprinted polymer and laminating the second molecularly imprinted polymer with a substrate S3 through the vinyl monomer. Specifically, living radical polymerization proceeds by formation of a polymerization reaction system in which the vinyl group introduced into the second molecularly imprinted polymer in the step 11, the vinyl monomer, and the second molecularly imprinted polymer as a template coexist on the surface of the substrate S3. The vinyl monomer is copolymerized with the vinyl groups of the functional monomers FM111 and FM112 introduced in the step 11 to form a polymer matrix (third molecularly imprinted polymer) around the protrusion of the second molecularly imprinted polymer.

The material of the substrate S3 is, for example, a metal, glass, or a resin, and is not particularly limited. Examples of the resin include poly(meth)acrylates, polystyrene, ABSs (acrylonitrile-butadiene-styrene copolymers), polycarbonate, polyesters, polyethylene, polypropylene, nylons, polyurethanes, silicone resins, fluorine resins, methylpentene resins, phenol resins, melamine resins, epoxy resins, and vinyl chloride resins. In the case of preparing a sensor substrate for optical analysis, the material is preferably transparent, and more preferably colorless and transparent. From this point of view, preferable examples of the material of the substrate S3 include colorless and transparent glass and colorless and transparent resins.

In the case that the substrate S2 is a metal substrate (that is not laminated with a glass substrate), the substrate S3 may be any of the above-described substrates, but from the viewpoint of facilitating the step 14 described below, the substrate S3 is preferably a metal substrate (that is not laminated with a glass substrate) or a resin. In the case that the substrate S2 is a glass substrate or a glass substrate having a metal thin film, the substrate S3 is a metal substrate (that is not laminated with a glass substrate) or a resin from the viewpoint of facilitating the step 14 described below.

The substrate S3 is preferably surface-modified by bonding a surface-modifying group in advance. For example, as shown in the drawings, a self-assembled monolayer (SAM) is preferably formed on the substrate S3 in advance. The SAM is stable and uniform because it is chemically bonded to the substrate S3 and because the molecules are closely and regularly aligned on the substrate S3 due to the intermolecular force. Hereinafter, a case in which a SAM is formed for surface modification of the surface of the substrate S3 will be described as a representative.

Examples of the molecule for formation of the SAM include straight-chain alkanes having 8 or more carbon atoms and having, at one terminal, a binding group to the surface of the substrate S3 (such as, in the case that the substrate S1 is a metal substrate, a thiol group or an acetic acid thioester group capable of binding to the surface of the metal substrate) and, at the other terminal, a polymerization-initiating group. In this case, the polymerization-initiating group functions as a polymerization initiator in the copolymerization reaction in the step 3 described below. The polymerization-initiating group with which the substrate S3 is surface-modified is to be different from the polymerization-initiating group used in the substrate S2.

In the case of using a metal substrate as the substrate S3, a SAM can be formed on the metal substrate by a conventional method. For example, a SAM is formed by dissolving SAM-forming molecules in a solvent such as ethanol, and immersing a metal substrate in the resulting solution at room temperature for 30 minutes or more and about 48 hours to bond each molecule to the surface of the metal substrate through a thioether bond, and to assemble the molecules closely while the molecules are oriented by intermolecular force. Alternatively, the SAM-forming molecule may be extended stepwise through the linker group exemplified in the step 1 described above. In this case, the polymerization-initiating group is to be introduced at the final terminal. Then, after removing the excess SAM-forming molecules by washing, the resulting product is to be dried.

In the case of using a glass substrate as the substrate S3, a SAM can be formed by introducing a reactive group such as an amino group onto the surface with a silane coupling agent such as 3-aminopropyltriethoxysilane (APTES).

The vinyl monomer to be added to the polymerization reaction system is not particularly limited as long as the vinyl monomer has a vinyl group structure copolymerizable with the vinyl groups introduced into the target substance in the step 11 (that is, the vinyl monomer groups of the functional monomer FM111 and the functional monomer FM112), and can be appropriately selected by those skilled in the art.

Preferable examples of the vinyl monomer include biocompatible monomers. The term "biocompatible monomer" refers to a monomer capable of forming a biocompatible polymer. A biocompatible polymer has an advantage, due to its excellent biocompatibility, that a sensor substrate is obtained that is suitable for analysis of a biological sample such as blood.

The biocompatible polymer is preferably a hydrophilic polymer, and more specifically a zwitterionic polymer. The zwitterionic monomer capable of forming a zwitterionic polymer includes, in one molecule, both an anionic group derived from an acidic functional group (such as a phosphate group, a sulfate group, or a carboxyl group) and a cationic group derived from a basic functional group (such as a primary amino group, a secondary amino group, a tertiary amino group, or a quaternary ammonium group). Examples of the zwitterionic monomer include phosphobetaines, sulfobetaines, and carboxybetaines, and phosphobetaines are more preferable.

Examples of the sulfobetaines include N,N-dimethyl-N-(3-sulfopropyl)-3'-methacryloylaminopropanaminium inner salt (SPB) and N,N-dimethyl-N-(4-sulfobutyl)-3'-methacryloylaminopropanaminium inner salt (SBB). Examples of the carboxybetaines include N,N-dimethyl-N-(1-carboxymethyl)-2'-methacryloyloxyethanaminium inner salt (CMB) and N,N-dimethyl-N-(2-carboxyethyl)-2'-methacryloyloxyethanaminium inner salt (CEB). Examples of the phosphobetaines include molecules having a phosphorylcholine group as the side chain, and 2-methacryloyloxyethyl phosphorylcholine (MPC) is more preferable.

The rate of the number of moles of the biocompatible monomer to the total amount of monomers is, for example, 50% or more, preferably 75% or more, more preferably 90% or more, and still more preferably 95% or more.

Examples of the vinyl monomer also include nonionic polymers. Nonionic polymers have an advantage that a sensor substrate is obtained in which non-specific adsorption is reduced. Examples of the nonionic polymers include vinyl monomers having a polyether-based polymer (such as poly (ethylene glycol)).

The vinyl monomer may contain a functional monomer FM12. The functional monomer FM12 has, for example, a specific structure as described below.

$$W—X—Q^{12} \tag{II}$$

In the above-described formula, W represents a vinyl monomer group, and X represents a single bond or a linker group. W and X are selected from the groups exemplified as W and the groups exemplified as X in the functional monomer FM1 described in the step 1, respectively.

$Q^{12}$ represents a binding group bg3' corresponding to the binding group bg3 in the protrusion-shaped polymer replica portion of the polymer replica substrate of the target substance. As the binding group bg3' corresponding to the binding group bg3, a group capable of forming a non-covalent bond (reversible linking group RV3) with the binding group bg3 can be appropriately determined by those skilled in the art preferably according to the kind of the binding group bg3. Specific examples of the binding group bg3' corresponding to the binding group bg3 can be selected from the non-covalent binding groups exemplified in the middle column of Table 1 (or in the third column of Table 2) described above. In the illustrated aspect, the binding group bg3 is assumed to be a carboxyl group that imitates the side chain carboxyl group of the protein moiety, and as the binding group bg3' corresponding to the binding group bg3, a basic group is used. The basic group can be selected from an amino group, cyclic secondary amino groups (such as a pyrrolidyl group and a piperidyl group), a pyridyl group, an imidazole group, and a guanidine group. Preferable examples of the basic group include secondary amino groups (such as a pyrrolidyl group and a piperidyl group), and a pyrrolidyl group is more preferable. The vinyl monomer containing such a functional monomer FM12 is copolymerized to obtain a third molecularly imprinted polymer in which the binding group bg3 in the protrusion-shaped polymer replica portion and the binding group bg3' derived from the functional monomer FM12 can form a hydrogen bond as the reversible linking group RV3.

In the polymerization reaction system, a crosslinking agent may be used in combination with the vinyl monomer. Examples of the crosslinking agent include compounds in which two or more vinyl monomer groups are bonded through a linker group. Specific examples of the crosslinking agent include compounds represented by the general formula W—X—W (in the formula, W represents a vinyl monomer group, and X represents a linker group). The vinyl monomer group W and the linker group X included in the crosslinking agent are the same as described above. More specific examples of the crosslinking agent include low molecular weight crosslinking agents such as N,N'-methylenebisacrylamide and ethylene glycol dimethacrylate. The crosslinking agent is used at a rate of the number of moles of the crosslinking agent to the total number of moles of the vinyl monomer and the crosslinking agent of, for example, 5% or more, preferably 10% or more, more preferably 15% or more, and still more preferably 18% or more from the viewpoint of the appropriate strength of the third imprinted polymer obtained by the crosslinking and/or the viewpoint of further accurate inheritance, by the second imprinted polymer, of the surface information of the second imprinted polymer as a template. From the viewpoint of controlling the hardness of the third imprinted polymer to be not too high so that the third imprinted polymer can be easily removed by separating the substrates in the step 13 described below, the rate of the number of moles of the crosslinking agent to the total number of moles of the vinyl monomer and the crosslinking agent is, for example, 30% or less, preferably 25% or less, and more preferably 22% or less. That is, the specific range of the rate of the number of moles of the crosslinking agent to the total number of moles of the vinyl monomer and the crosslinking agent is, for example, 5 to 30%, 5 to 25%, 5 to 22%, 10 to 30%, 10 to 25%, 10 to 22%, 18 to 30%, 18 to 25%, or 18 to 22%.

The polymerization reaction system preferably further includes, as a polymerization catalyst, a transition metal or a transition metal complex including a transition metal compound and a ligand, and more preferably further includes a reducing agent to be used. As the transition metal complex and the reducing agent, those described in the step 3 can be used.

The copolymerization condition in the step 12 is appropriately determined by those skilled in the art. For example, the biocompatible polymer is water-soluble, and therefore in the presence of an aqueous solvent, a vinyl monomer is added to the second molecularly imprinted polymer on the substrate S2, and a polymerization initiator is used (in the case that the SAM having a polymerization-initiating group is formed on the surface of the substrate S3, the polymerization-initiating group may be used) to initiate polymerization. A reaction solution is filled between the surface of the second molecularly imprinted polymer and the substrate S3 laminated thereto. The polymerization temperature may be 0° C. or more and 120° C. or less, and preferably room temperature (5° C. or more and 35° C. or less, preferably 10° C. or more and 30° C. or less), and the polymerization time can be about 10 minutes or more and 50 hours or less. After the copolymerization reaction, the substrate is preferably washed with the used solvent or the like to remove the excess reagent.

[Step 13: Removal of Second Molecularly Imprinted Polymer]

In the step 13, the reversible linking group RV1 and the reversible linking group RV2 are cleaved and the second molecularly imprinted polymer is removed. As a result, a negative third molecularly imprinted polymer is obtained that includes a recess generated using the second molecularly imprinted polymer as a template and includes a binding group bg1' and a binding group bg2' as cleavage residues on the surface of the recess. In the illustrated aspect, the reversible linking group RV3 is also cleaved in addition to the reversible linking group RV1 and the reversible linking group RV2 to obtain a second molecularly imprinted polymer including also the binding group bg3' in addition to the binding group bg1' and the binding group bg2'. The binding group bg1', the binding group bg2', and the binding group bg3' are a cleavage residue of the reversible linking group RV1, a cleavage residue of the reversible linking group RV2, and a cleavage residue of the reversible linking group RV3, respectively, and specific examples thereof are listed in the third column of Table 2.

The way of cleavage of the reversible linking group can be appropriately determined by those skilled in the art according to the kind of each reversible linking group. For example, in the case that the reversible linking group RV1, the reversible linking group RV2, and the reversible linking group RV3 are a disulfide bond, a boronate-cis-diol ester group, and a hydrogen bond respectively as illustrated in the drawings, the reversible linking groups are to be subjected to a condition for reduction of the disulfide bond and the boronate-cis-diol ester group. More specifically, the composite of the substrate S2, the second molecularly imprinted polymer on the substrate S2, the substrate S3, and the third molecularly imprinted polymer on the substrate S3 obtained in the step 12 are to be immersed in a liquid containing a reducing agent at room temperature in an appropriate solvent. Examples of the reducing agent include tris (2-carboxyethylphosphine) (TCEP), dithiothreitol (DTT), and tributylphosphine (TBP). As a result, the covalent binding reversible linking group RV1 and reversible linking group RV2 are cleaved, and the hydrogen-bonding reversible linking group RV3 is also cleaved. After the reduction reaction, the substrate S2 (and the second molecularly imprinted polymer on the substrate S2) and the substrate S3 (and the third molecularly imprinted polymer on the substrate S3) are separated.

In this way, a third molecularly imprinted polymer can be obtained that has a recess formed as a space for molecular imprinting using the protrusion-shaped polymer replica portion of the second molecularly imprinted polymer as a template. Because the second molecularly imprinted polymer accurately imitates the functional group information on the surface of the object substance, the recess of the third molecularly imprinted polymer can function as a specific recognition site for the target substance (that is, a space in which the target substance can be specifically taken).

[Step 14: Introduction of Post-Imprinting Compound and/or Signal Substance]

In the step 14, a post-imprinting compound and/or a signal substance capable of interacting with at least one of a binding group BG1 or a binding group BG2 is bonded to at least one of the binding group bg1' or the binding group bg2'. The post-imprinting compound and/or the signal substance is preferably bonded to the binding group that corresponds to the binding group of the target substance and is different from the binding group of the target substance. In order to obtain a further large effect of bonding the post-imprinting compound and/or the signal substance, the post-imprinting compound and/or the signal substance is preferably bonded to one of a plurality of binding groups bg1' or a plurality of binding groups bg2' in the specific recognition space (recess) (in the illustrated aspect, to the binding group bg1').

In the case of the post-imprinting compound, the post-imprinting compound bonded in the specific recognition space (recess) interacts with the binding group of the target substance when the target substance is recognized in the specific recognition space to improve the affinity and/or selectivity of the specific recognition space for the target substance.

For example, when the post-imprinting compound is bonded to the binding group bg1' that corresponds to the binding group of the target substance and is different from the binding group of the target substance, the position of the bonded post-imprinting compound corresponds to the position of the binding group BG1 of the target substance to be detected that enters the specific recognition space. Therefore, when the target substance enters the specific recognition space during use of the substrate sensor, the post-imprinting compound and the binding group BG1 of the target substance interact with each other. Thus, the selectivity and the affinity of the specific recognition space for the target substance are improved.

The post-imprinting compound has a binding group corresponding to the binding group BG1 of the target substance. Examples of such a binding group include the binding groups shown in the middle column of Table 1 described above. From the viewpoint of obtaining a further good effect based on the positions of the binding group BG1 and the post-imprinting compound, such a binding group is preferably bonded through the linker group represented by Z in the formula (I) in the above-described step 1.

The signal substance remarkably improves the detection sensitivity to the target substance as follows. When the target substance is recognized in the specific recognition space (recess), the signal intensity derived from the signal substance in the specific recognition space changes or the spectrum changes (for example, the peak shifts), so that the presence or absence of the target substance or its concentration in the sample to be analyzed can be easily measured.

The signal substance is not particularly limited as long as, specifically, it has a size that does not prevent the insertion of the target protein into the specific recognition space. Furthermore, the signal substance can be used without particular limitation as long as when the target substance enters the specific recognition site, the detected signal intensity changes or the spectrum changes (for example, the peak shifts). Examples of the signal substance include fluorescent substances, radioactive element-containing substances, and magnetic substances. From the viewpoint of detectability and the like, the signal substance is preferably a fluorescent substance. Examples of the fluorescent substance include cyanine-based dyes such as a fluorescein-based dye and an indocyanine dye, and fluorescent dyes such as a rhodamine-based dye. Examples of the radioactive element-containing substances include sugars, amino acids, and nucleic acids labeled with a radioisotope such as $^{18}F$. Examples of the magnetic substances include substances having a magnetic material such as ferrichrome, and substances found in ferrite nanoparticles, nanomagnetic particles, and the like.

The signal substance can also be configured as one constituent of a fluorescent dye pair that causes fluorescence resonance energy transfer (FRET). The fluorescent dye pair that causes FRET is not particularly limited, and whether a donor dye or an acceptor dye is selected as the signal substance is not particularly limited. A donor dye can be preferably selected as the signal substance. Specific examples of the donor dye and the acceptor dye as the constituents of the fluorescent dye pair that causes FRET include fluorescein isothiocyanate (FITC) and tetramethylrhodamine isothiocyanate (TRITC), Alexa Fluor647 and Cy5.5, HiLyte Fluor647 and Cy5.5, and R-phycoerythrin (R-PE) and allophycocyanin (APC).

In this way, a sensor substrate is obtained that has the substrate S3, the third molecularly imprinted polymer, provided on the substrate S3, having the specific recognition site of the target substance, and the post-imprinting compound and/or the signal substance bonded to the specific recognition site. The method for producing a sensor substrate according to the present invention enables preparation of a molecular recognition material for a target substance by using a polymer replica substrate that accurately imitates the functional group information on the surface of the object substance as a template without using the target substance as a template. The template includes a synthetic polymer, therefore, the sensor substrate can be produced extremely efficiently due to the chemical stability, the physical stability, and the further improved economical efficiency of the template. As a result, analysis tools and analysis kits used in the medical field, the environment/water analysis field, the food field, and the like can be easily produced.

[Analysis of Target Substance]

To analyze a target substance using a substrate sensor, an analysis sample solution containing the target substance is brought into contact with the surface of the substrate sensor.

The analysis sample solution is not particularly limited, and may be a solution prepared through a purification or crude purification treatment of the target substance, or a solution prepared without such a treatment. Examples of the treatment include ultracentrifugation, ultrafiltration, continuous flow electrophoresis, filtration in which a size filter is used, and gel filtration chromatography. Specific examples of the analysis sample solution include biological samples (body fluid samples such as blood, milk, urine, saliva, lymph, cerebrospinal fluid, amniotic fluid, tears, sweat, and nasal flow), environment/water samples, and food samples.

When the analysis sample containing the target substance is brought into contact with the surface of the substrate sensor, the target substance is specifically captured by the specific recognition site on the surface of the substrate sensor. In the case of the specific recognition site to which a signal substance is bonded, the target substance specifically captured by the specific recognition site shields the signal substance, so that the signal intensity detected from the signal substance is changed. By this change in signal intensity, the target substance is detected.

In the case that the signal substance in the substrate sensor is configured as one constituent of a fluorescent dye pair that causes fluorescence resonance energy transfer (FRET), one constituent of the fluorescent dye pair is previously bonded to the target substance in the analysis sample. In this case, when the target substance is specifically captured by the specific recognition site, the fluorescent dye of the signal substance and the fluorescent dye of the target substance close with each other, so that fluorescence is emitted by FRET. By this fluorescence emission by FRET, the target substance is detected.

EXAMPLES

Hereinafter, the present invention will be described in detail with reference to Examples, but the present invention is not limited thereto.

Introduction of Vinyl Group into Target Substance AFP (Step 1)

An AFP solution (AFP Liquid in tris buffered saline, pH 7.5 with sodium azide, manufactured by Lee Biosolutions, Inc.) was ultrafiltrated (4° C., 14,000×g, 10 minutes), and the AFP was redispersed in a 10 mM phosphate buffer (pH 7.4) so that the concentration of AFP was 1 mg/mL. In an Eppendorf tube, 200 μL (200 μg, 2.9 nmol) of the resulting solution was put, 1 mg/mL of a functional monomer FM1 solution (10 mM phosphate buffer (pH 7.4)) was added so that the amount of the functional monomer FM1 (molecular weight (M.W.)=449.45) was 10 equivalents with respect to the AFP, and the resulting mixture was reacted at 4° C. for 14 hours. After the reaction, the mixture was diluted with a 10 mM phosphate buffer (pH 7.4) using Amicon Ultra-0.5 (molecular weight cutoff (MWCO): 30 kDa) to remove the unreacted FM1, and ultrafiltrated (4° C., 14,000×g, 10 minutes) 3 times. The number of the introduced FM1s was calculated from the peak shift of matrix-assisted laser desorption/ionization time-of-flight mass spectrometry (MALDI-TOF-MS) (matrix: sinapinic acid, method: IgG liner).

Modification of Gold Substrate

A surface plasmon resonance (SPR) gold substrate washed with ethanol was subjected to UV-$O_3$ cleaning for 20 minutes. The gold substrate was immersed (30° C., 18 h) in an EtOH solution (2 mL) in which amino-$EG_6$-untecanthiol (molecular weight (Mw): 504.16) and bis[2-(2-bromoisobutyryloxy)undecyl]disulfide (Mw: 704.7) were dissolved as compounds for formation of a SAM so that the concentration of each compound was 0.5 mM, and the gold substrate was surface-modified with the SAM (mixed-SAM) having an amino group and an atom transfer radical polymerization (ATRP) initiating group as terminal groups. The modified gold substrate was washed with EtOH and Milli-Q water and dried with $N_2$. The dried substrate was stored in a vacuum desiccator. Furthermore, in order to introduce a phenylboronic acid group into the amino group, 3-fluoro-4-carboxyphenylboronic acid (CFPBA) and 4-(4,6-dimethoxy-1,3,5-triazine-2-yl)-4-methylmorpholinium chloride (DMT-MM)

were dissolved in EtOH (2 mL) so that the concentration of the CFPBA was 1 mM and the concentration of the DMT-MM was 10 mM, and the substrate modified with the mixed-SAM was immersed in the resulting solution and incubated at 25° C. for 3 hours. After the reaction, the substrate was washed with MeOH and Milli-Q water and dried with $N_2$.

Immobilization of Target Substance AFP (Step 2)

Onto the obtained substrate modified with the mixed-SAM, 100 μL of a 10 μg/mL FM1-AFP solution was added dropwise, and the resulting product was incubated at 25° C. for 1 hour. Then, the substrate was washed with a phosphate buffer solution to obtain an AFP-immobilized gold substrate.

Synthesis of First Molecularly Imprinted Polymer (1st MIP) (Step 3)

Pyridinium methacrylate (PyM; 250 μM), acrylamide (AAm, 40 mM), and N,N'-methylenebisacrylamide (MBAA; 10 mM) were dissolved in 4.5 mL of a 10 mM phosphate buffer (pH 7.4), 2,2-bipyridine (2 mM) and $CuBr_2$ (1 mM) were further added, and the resulting solution was subjected to freezing-degassing-nitrogen replacement to prepare a prepolymer solution. Separately, an ascorbic acid (6.25 mM) Milli-Q aqueous solution was prepared, and subjected to freezing-degassing-nitrogen replacement in the same manner. The AFP-immobilized gold substrate was put in a Schlenk flask, the prepolymer solution was added, degassing and nitrogen replacement was sufficiently performed, an ascorbic acid solution (400 μL) was added with a syringe, and degassing and nitrogen replacement was performed again. Then, the flask was immersed in a water bath set at 40° C. to carry out a surface-initiated atom transfer radical polymerization reaction for 1 hour. After the polymerization, the substrate was washed with Milli-Q water and stored in a 10 mM phosphate buffer.

Removal of Template (AFP) (Step 4)

In order to remove copper, the substrate after the polymerization was immersed in 5 mL of a 50 mM EDTA-4Na aqueous solution and reacted at 25° C. for 1 hour while shaken. Then, in order to reduce the disulfide bond and remove the template AFP after the polymerization, the resulting product was immersed in 5 mL of a 20 mM TCEP aqueous solution and reacted at 25° C. for 5 hours while shaken.

Introduction of Vinyl Group into Template (First Molecularly Imprinted Polymer) (Step 5)

In order to introduce a vinyl group into the first molecularly imprinted polymer (1st MIP) using a disulfide exchange reaction, 100 μL of a 1 mM pyridyldithioethyl methacrylamide solution (50% MeOH, v/v) was added dropwise and reacted (25° C., over night). After washing with 50% MeOH (v/v) and a phosphate buffer, 100 μL of a 1 mM glycosylethyl methacrylamide (GMA) solution (10 mM phosphate buffer, pH 7.4) was further added dropwise and reacted at 25° C. for 1 hour.

Modification of Gold Substrate

A washed gold substrate manufactured by JASCO Corporation was covered with a silicon sheet, and 100 μL of an EtOH solution in which 1.0 mM iniferter-SH (represented by the following formula, Mw: 392.7) was dissolved was added dropwise to surface-polymerize the gold substrate with a polymerization-initiating group (30° C., 18 h). The modified gold substrate was washed with EtOH and dried with $N_2$.

[Chem. 2]

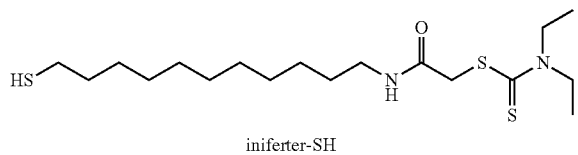

iniferter-SH

Synthesis of Second Molecularly Imprinted Polymer (2nd MIP) (Step 6)

Acrylic acid (1 mM), 2-methacryloyloxyethyl phosphorylcholine (MPC; 40 mM), and N,N'-methylenebisacrylamide (MBAA; 10 mM) were dissolved in a 10 mM phosphate buffer (pH 7.4), and the resulting solution was subjected to freezing-degassing-nitrogen replacement. Onto the first molecularly imprinted polymer, 100 μL of the prepolymer solution was added dropwise, and then the resulting product was laminated with the gold substrate and subjected to a polymerization reaction under a nitrogen flow using Key-Chem-Lumino (ultraviolet light emitting LED, peak wavelength 365 nm) for 3 hours.

Removal of Template (First Molecularly Imprinted Polymer) (Step 7)

The laminate after the polymerization reaction was immersed in a 20 mM TCEP aqueous solution at 25° C. for 3 hours to separate the substrates. As a result, a polymer replica substrate of the target substance AFP was obtained.

Introduction of Vinyl Group into Second Molecularly Imprinted Polymer (Step 11)

In order to introduce a vinyl group into the second molecularly imprinted polymer (2nd MIP) of the polymer replica substrate using a disulfide exchange reaction, 100 μL of a 1 mM pyridyldithioethyl methacrylamide solution (50% MeOH, v/v) was added dropwise and reacted (25° C., over night). After washing with 50% MeOH (v/v) and a phosphate buffer, 100 μL of a 1 mM 3-fluoro-4-carboxyphenyl-boronic acid (CFPBA) solution (10 mM phosphate buffer, pH 7.4) was further added dropwise and reacted at 25° C. for 1 hour. Then, the resulting product was washed once with 100 μL of a phosphate buffer.

Surface Modification of Glass Substrate

A 25 mm square glass substrate (thickness: about 0.5 mm) was washed with a piranha solution (concentrated $H_2SO_4$: $H_2O_2$=3:1, v/v) for 30 minutes, and washed by pouring MeOH, pure water, and EtOH. Immediately, the substrate was immersed in a 1 w % APTES solution prepared in a plastic petri dish, and allowed to stand at 25° C. for 1 hour. Then, the substrate was washed by pouring EtOH, and fired on a hot plate at 110° C. for 15 minutes to aminate the surface of the glass substrate. The resulting substrate was immersed in a DMSO solution in which 2-bromoisobutyric acid (5 mM), EDC (7.5 mM), and NHS (7.5 mM) were dissolved, and reacted at 25° C. for 2 hours for bromination. Then, the substrate was washed by pouring DMSO and EtOH, and dried with an $N_2$ gas. The obtained Br-modified glass substrate was cut into 12.5 mm squares and used for polymerization reaction.

Synthesis of Third Molecularly Imprinted Polymer (3rd MIP) (Step 12)

Pyridinium methacrylate (PyM; 1 mM), 2-methacryloyloxyethyl phosphorylcholine (MPC; 40 mM), N,N'-methylenebisacrylamide (MBAA; 10 mM), 2,2-bipyridine (2 mM), and $CuBr_2$ (1 mM) were dissolved in a 10 mM phosphate buffer (pH 7.4) (so that the total amount was 500 μL), and the resulting solution was subjected to freezing-degassingnitrogen replacement to prepare a monomer solution. Separately, an ascorbic acid (6.25 mM) Milli-Q aqueous solution was prepared, and subjected to freezing-degassing-nitrogen replacement in the same manner. Both the solutions were put in a glove box and the inside of the container was replaced with nitrogen. Then, 40 µL of an ascorbic acid aqueous solution was added to the monomer solution and mixed, 100 µL of this prepolymer solution was added dropwise onto the second molecularly imprinted polymer of the polymer replica substrate, then the resulting product was laminated with the glass substrate surface-modified with a bromo group and put in an Erlenmeyer flask, and the flask was sealed with a septum. The laminate was taken out of the glove box and subjected to degassing and nitrogen replacement again, 100 µL of a mixed solution of the monomer solution and an ascorbic acid aqueous solution separately subjected to degassing and nitrogen replacement was further added, and the resulting product was subjected to degassing and nitrogen replacement, then immersed in a water bath at 40° C., and allowed to stand to carry out a polymerization reaction for 1 hour.

Removal of Template (Second Molecularly Imprinted Polymer) (Step 13)

In order to remove copper, the substrate after the polymerization was immersed in a 50 mM EDTA-4Na aqueous solution and reacted at 25° C. for 1 hour while shaken. Then, the substrate was immersed in a 20 mM TCEP aqueous solution (25° C., over night) to separate the substrates.

Introduction of Fluorescent Molecule (Step 14)

After removing the template molecule, 100 µL of a 1 mM aqueous solution of a rhodamine fluorescent reagent in which a disulfide group was introduced (50% MeOH, v/v) was added dropwise onto the substrate, and the resulting product was reacted at 25° C. over night in a state of being covered with a cover glass. The substrate after the reaction was washed with MeOH and pure water. As a result, a substrate sensor was obtained.

Evaluation of AFP (Target Substance) Binding Ability of Sensor Substrate AFP

1. AFP Binding Ability Test of First Molecularly Imprinted Polymer (1st MIP)

Reference Example

The first molecularly imprinted polymer substrate obtained in the step 4 was set on a surface plasmon resonance measuring device, and then a running buffer was fed until the baseline was stabilized. After stabilization, a 20 mM TCEP aqueous solution was injected (200 µL: 10 min), then the substrate was washed with 1% TRITON X-100 phosphate buffer solution (20 µL: 1 min), a 1 M NaCl aqueous solution (20 µL: 1 min), and a Glycine-HCl solution (20 µL: 1 min). When the RU value did not decrease any more, an AFP (10 mM phosphate buffer (pH 7.4)) solution was injected at a concentration of 0 ng/mL, 0.5 ng/mL, 1 ng/mL, 5 ng/mL, 10 ng/mL, 50 ng/mL, and 100 ng/mL (0 nM, 0.007 nM, 0.014 nM, 0.072 nM, 0.14 nM, 0.72 nM, and 1.45 nM) to perform SPR measurement.

For the measurement, the following method was adopted in the device, and the AFP solution was injected stepwise with an autosampler.

Running buffer: 10 mM phosphate buffer (pH 7.4)
Flow rate: 20 µL/min, contact time: 1 minute (injection volume: 20 µL)
Set temperature: 25° C.
(1) The running buffer was fed, and the value 5 minutes after the start of feeding was obtained as a baseline value.

(2) The protein was injected (1 min). The value 5 minutes after the end of injection was obtained as a data point value.

(3) The protein having the next highest concentration was injected. The value 5 minutes after the end of injection was obtained as a data point value. The difference between the baseline value and the data point value of each protein was adopted as the ΔRu value.

Figure 7:
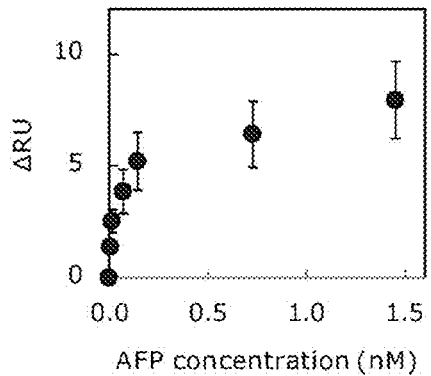
FIG. 7 is an adsorption isotherm obtained in α-fetoprotein (AFP) detection by surface plasmon resonance (SPR) using a first molecularly imprinted polymer (prepared using a target substance AFP as a template), the adsorption isotherm showing the change in the SPR signal with respect to the AFP concentration.

FIG. 7 is an adsorption isotherm obtained in AFP detection by SPR using the first molecularly imprinted polymer substrate (prepared using the target substance AFP as a template). The adsorption isotherm shows the change in the SPR signal with respect to the AFP concentration. The binding constant was calculated from the obtained adsorption isotherm using curve fitting software to be $K_d=6.2\times10^{-11}$ [M].

2. AFP Binding Ability Test of Third Molecularly Imprinted Polymer (3rd MIP)

Example

The sensor substrate having the third molecularly imprinted polymer obtained in the step 14 was put in a glass bottom dish and immersed in 3 mL of a 10 mM phosphate buffer (pH 7.4). An AFP solution was added in an amount of 3 µL at a concentration of 0.5 µg/mL, 1 µg/mL, 5 µg/mL, 10 µg/mL, 50 µg/mL, and 100 µg/mL (final concentration of 0 ng/mL, 0.5 ng/mL, 1 ng/mL, 5 ng/mL, 10 ng/mL, 50 ng/mL, and 100 ng/mL (0 nM, 0.007 nM, 0.014 nM, 0.072 nM, 0.14 nM, 0.72 nM, and 1.45 nM)), the resulting product was incubated while stirred with a magnetic stirrer for 20 minutes, and the fluorescence intensity of the substrate at each AFP concentration was measured with a fluorescence microscope. The measurement conditions were as follows. The light quantity was 100%, the magnification of the objective lens was 4 times, the filter was Cy3, the exposure time was 0.1 seconds, the bit number was 16, and the measurement points were 9 points of 50×50 pixels in the substrate.

The substrate before the introduction of the fluorescent molecule obtained in the step 13 was also put in a glass bottom dish and immersed in 3 mL of a 10 mM phosphate buffer (pH 7.4), and measured (Comparative Example).

Figure 8:
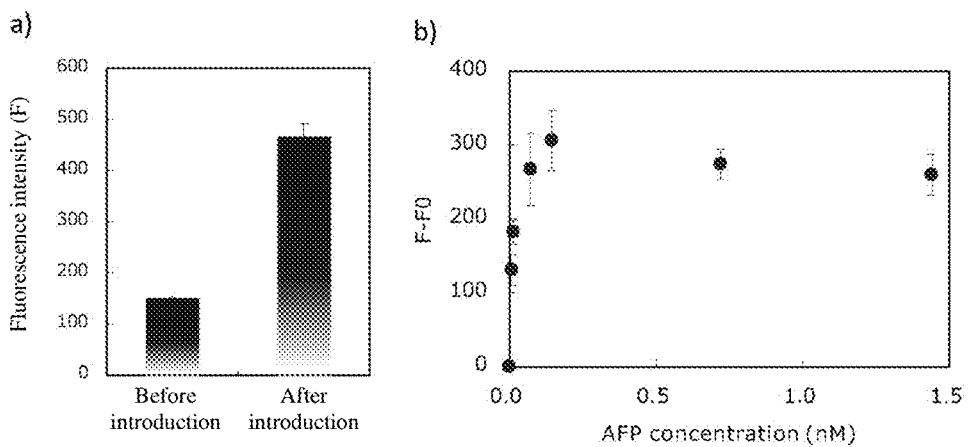
FIG. 8, (a) shows a comparison of the fluorescence intensity between a substrate before introduction of a fluorescent molecule (a comparative example) and a substrate after the introduction (an example: a substrate sensor according to an embodiment of the present invention), and FIG. 8, (b) is an adsorption isotherm obtained in AFP detection by fluorescence microscope measurement using a substrate sensor having a third molecularly imprinted polymer (prepared using, as a template, a polymer replica substrate having a second molecularly imprinted polymer), the adsorption isotherm showing the change in the fluorescence intensity with respect to the AFP concentration.

FIG. 8, (a) shows a comparison of the fluorescence intensity between the substrate before the introduction of the fluorescent molecule (Comparative Example) and the substrate after the introduction (Example). FIG. 8, (b) is an adsorption isotherm obtained in AFP detection by fluorescence microscope measurement using the substrate sensor having the third molecularly imprinted polymer (prepared using, as a template, the polymer replica substrate having the second molecularly imprinted polymer). The adsorption isotherm shows the change in the fluorescence intensity with respect to the AFP concentration. The binding constant was calculated from the obtained adsorption isotherm using curve fitting software to be $K_d=1.2\times10^{-11}$ [M].

Evaluation of Selectivity of Substrate Sensor

Figure 9:
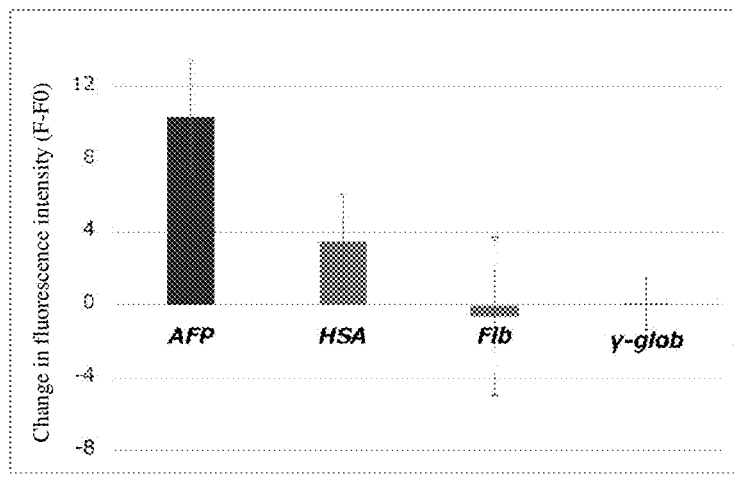
FIG. 9 shows a result of a protein selective adsorption test on a substrate sensor according to an embodiment of the present invention.

The sensor substrate having the third molecularly imprinted polymer obtained in the step 14 was put in a glass bottom dish and immersed in 3 mL of a 10 mM phosphate buffer (pH 7.4). AFP was added so that the final concentration was 1.45 nM, the resulting product was incubated while stirred with a magnetic stirrer for 20 minutes, and then the fluorescence intensity of the substrate sensor was measured with a fluorescence microscope. The substrate after the AFP adsorption test was washed with a 10 mM Gly-HCl buffer (pH 2.5, 3 mL, while stirred for 5 minutes) 3 times, a 0.5 wt % SDS aqueous solution (3 mL, while stirred for 5 minutes) 3 times, and a 10 mM phosphate buffer (pH 7.4, 3 mL, while stirred for 5 minutes) 3 times. Subsequently, as a control protein, HSA (66.5 kDa), fibrinogen (340 kDa), and γ-globrin (from human blood) (150 kDa) were each also added so that the final concentration was 1.45 nM, the same operation as in the case of AFP was performed for each protein, the fluorescence intensity of the substrate sensor was measured, and the substrate was washed. FIG. 9 shows the result of the protein adsorption test.

DESCRIPTION OF REFERENCE SIGNS

BG1, BG2, BG3: Binding group (of target substance)
bg1, bg2, bg3: Binding group
bg1', bg2', bg3': Binding group
RV1, RV2, RV3: Reversible linking group
FM1, FM3, FM51, FM52, FM6, FM12, FM111, FM112: Functional monomer
S1, S2, S3: Substrate

The invention claimed is:

1. A polymer replica of a target substance, the target substance having a plurality of kinds of binding groups including at least a binding group BG1 and a binding group BG2 on a surface, the polymer replica comprising a second molecularly imprinted polymer produced with a first molecularly imprinted polymer as a template, the first molecularly imprinted polymer produced with the target substance as a template, the polymer replica having on a surface, at least:
a binding group bg1 at a position corresponding to a position of the binding group BG1 on the surface of the target substance; and
a binding group bg2 at a position corresponding to a position of the binding group BG2 on the surface of the target substance.

2. The polymer replica of the target substance according to claim 1, further comprising a substrate and a polymer film having a protrusion, the polymer film provided on a surface of the substrate, the protrusion including the second molecularly imprinted polymer.

3. The polymer replica of the target substance according to claim 1, wherein:
the target substance is a protein,
the binding group BG1 and the binding group BG2 are at least two kinds of groups selected from the group consisting of a carboxyl group, an amino group, and sugar groups, and
the binding group bg1 and the binding group bg2 are at least two kinds of groups selected from the group consisting of a carboxyl group, a thiol group, and sugar groups.

4. A method for producing a polymer replica of a target substance, the method comprising:
a step 1 of bonding a functional monomer FM1 having a vinyl group and a reversible linking group RV1 to a target substance having a plurality of kinds of binding groups on a surface through at least a binding group BG1 among the plurality of kinds of binding groups;
a step 2 of reacting a binding group BG2 among the plurality of kinds of binding groups on a substrate S1 and immobilizing the target substance through a reversible linking group RV2;
a step 3 of performing molecular imprinting by adding a vinyl monomer onto the substrate S1 and copolymerizing the vinyl monomer with the vinyl group;
a step 4 of cleaving the reversible linking group RV1 and the reversible linking group RV2 and removing the target substance to obtain a first molecularly imprinted polymer that includes a recess generated using the target substance as a template and includes a binding group bg1' and a binding group bg2' on a surface of the recess, the binding group bg1' and the binding group bg2' each being a cleavage residue;
a step 5 of:
reacting the binding group bg1' of the first molecularly imprinted polymer with a functional monomer FM51 that has a reactive group capable of reacting with the binding group bg1' to form a reversible linking group RV1 and has a vinyl group, and
reacting the binding group bg2' of the first molecularly imprinted polymer with a functional monomer FM52 that has a reactive group capable of reacting with the binding group bg2' to form a reversible linking group RV2 and has a vinyl group;
a step 6 of performing molecular imprinting by adding a vinyl monomer onto the first molecularly imprinted polymer and copolymerizing the vinyl monomer with the vinyl group of the functional monomer FM51 and with the vinyl group of the functional monomer FM52; and
a step 7 of cleaving the reversible linking group RV1 and the reversible linking group RV2 and removing the first molecularly imprinted polymer to obtain a second molecularly imprinted polymer having a binding group bg1 and a binding group bg2, the binding group bg1 and the binding group bg2 each being a cleavage residue.

5. The method according to claim 4, wherein:
step 6 is a step of performing molecular imprinting by adding the vinyl monomer onto the first molecularly imprinted polymer, laminating the first molecularly imprinted polymer with a substrate S2 through the vinyl monomer, and copolymerizing the vinyl monomer with the vinyl group of the functional monomer FM51 and with the vinyl group of the functional monomer FM52, and
step 7 is a step of cleaving the reversible linking group RV1 and the reversible linking group RV2 and removing the first molecularly imprinted polymer to obtain a second molecularly imprinted polymer having the substrate S2 and having a binding group bg1 and a binding group bg2 on a surface of the substrate S2, the binding group bg1 and the binding group bg2 each being a cleavage residue.

6. The method according to claim 4, wherein:
the target substance is a protein,
in step 3, the vinyl monomer contains a functional monomer FM3 having a basic group and a vinyl group, and
in step 6, the vinyl monomer contains a functional monomer FM6 having an acidic group bg3 and a vinyl group.

7. The method according to claim 4, wherein the binding group BG1 is an amino group.

8. The method according to claim 4, wherein the reversible linking group RV1 is a disulfide group, and the binding group bg1 is a thiol group.

9. The method according to claim 4, wherein
the protein is a glycoconjugate, and
the binding group BG2 is a sugar group, the reversible linking group RV2 is a boronate-cis-diol ester group, and the binding group bg2 is a boronic acid group.

10. A polymer replica of a target substance, the polymer replica produced by the method according to claim 4.

11. A method for producing a substrate sensor, the method comprising:

a step 11 of, on a surface of the second molecularly imprinted polymer on the substrate of the polymer replica of the target substance according to claim 2:

reacting the binding group bg1 with a functional monomer FM111 that has a reactive group capable of reacting with the binding group bg1 to form a reversible linking group RV1 and has a vinyl group, and reacting the binding group bg2 with a functional monomer FM112 that has a reactive group capable of reacting with the binding group bg2 to form a reversible linking group RV2 and has a vinyl group;

a step 12 of performing molecular imprinting by adding a vinyl monomer onto the second molecularly imprinted polymer on the substrate, laminating the second molecularly imprinted polymer with a substrate S3 through the vinyl monomer, and copolymerizing the vinyl monomer with the vinyl group of the functional monomer FM111 and with the vinyl group of the functional monomer FM112;

a step 13 of cleaving the reversible linking group RV1 and the reversible linking group RV2 and separating the substrate of the polymer replica of the target substance to obtain a third molecularly imprinted polymer having the substrate S3, having a recess generated using the second molecularly imprinted polymer as a template, and having a binding group bg1' and a binding group bg2' on a surface of the recess, the binding group bg1' and the binding group bg2' each being a cleavage residue; and a step 14 of bonding a post-imprinting compound and/or a signal substance capable of interacting with at least one of a binding group BG1 or a binding group BG2 to at least one of the binding group bg1' or the binding group bg2'.

12. The method according to claim 11, wherein
the target substance is a protein, and
in step 12, the vinyl monomer contains a functional monomer FM12 having a basic group and a vinyl group.

13. The method according to claim 11, wherein the binding group BG1 is an amino group.

14. The method according to claim 11, wherein the reversible linking group RV1 is a disulfide group, and the binding group bg1' is a thiol group.

15. The method according to claim 11, wherein:
the protein is a glycoconjugate, and
the binding group BG2 is a sugar group, the reversible linking group RV2 is a boronate-cis-diol ester group, and the binding group bg2' is a boronic acid group.

* * * * *